(12) United States Patent
Vargas Rincon et al.

(10) Patent No.: US 10,512,613 B2
(45) Date of Patent: **\*Dec. 24, 2019**

(54) METHODS AND COMPOSITIONS PARTICULARLY FOR TREATMENT OF ATTENTION DEFICIT DISORDER

(71) Applicant: Purdue Pharma L.P., Stamford, CT (US)

(72) Inventors: Ricardo Alberto Vargas Rincon, Mississauga (CA); Joseph Reiz, Markham (CA)

(73) Assignee: PURDUE PHARMA L.P., Stamford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/399,580

(22) Filed: Apr. 30, 2019

(65) Prior Publication Data

US 2019/0254982 A1 Aug. 22, 2019

Related U.S. Application Data

(63) Continuation of application No. 16/120,999, filed on Sep. 4, 2018, now Pat. No. 10,292,939, which is a continuation of application No. 15/958,413, filed on Apr. 20, 2018, now Pat. No. 10,111,839, which is a (Continued)

(30) Foreign Application Priority Data

Aug. 27, 2015 (CA) ...................................... 2902911

(51) Int. Cl.
| | |
|---|---|
| A61K 9/50 | (2006.01) |
| A61P 25/00 | (2006.01) |
| A61K 47/06 | (2006.01) |
| A61K 31/4458 | (2006.01) |
| A61P 25/26 | (2006.01) |
| A61K 9/48 | (2006.01) |
| A61K 9/16 | (2006.01) |
| A61K 9/14 | (2006.01) |

(52) U.S. Cl.
CPC .............. *A61K 9/5078* (2013.01); *A61K 9/14* (2013.01); *A61K 9/1676* (2013.01); *A61K 9/48* (2013.01); *A61K 9/5026* (2013.01); *A61K 9/5036* (2013.01); *A61K 9/5084* (2013.01); *A61K 31/4458* (2013.01); *A61K 47/06* (2013.01); *A61P 25/00* (2018.01); *A61P 25/26* (2018.01)

(58) Field of Classification Search
CPC .............. A61K 31/4458; A61K 9/5084; A61K 2300/00; A61K 9/5026; A61K 9/5078; A61K 9/2081; A61K 31/485; A61K 9/2086; A61K 9/5047; A61K 9/5073; A61K 9/0053; A61K 9/167; A61K 9/1676; A61K 9/209; A61K 9/2846; A61K 9/2893; A61K 9/5089; A61K 9/14; A61K 9/2054; A61K 9/2059; A61K 9/4808; A61K 9/5036; A61K 47/06; A61K 9/48; A61K 31/137; A61K 31/165; A61K 31/435; A61K 31/44; A61K 45/06; A61K 9/146; A61K 9/2009; A61K 9/2077; A61K 9/2853; A61K 31/663; A61K 47/58; A61K 47/585; A61K 9/0056; A61K 9/0065; A61K 9/2027; A61K 9/205; A61K 9/284; A61K 9/286; A61K 9/2866; A61K 9/50; A61K 9/5042; A61K 9/145; A61P 25/00; A61P 25/26; C12N 9/2402

See application file for complete search history.

(56) References Cited

U.S. PATENT DOCUMENTS

| | | | |
|---|---|---|---|
| 2,377,237 | A | 5/1945 | James |
| 2,507,631 | A | 5/1950 | Hartmann et al. |
| 2,676,169 | A | 4/1954 | Baldoni |

(Continued)

FOREIGN PATENT DOCUMENTS

| | | |
|---|---|---|
| AU | 1632692 A | 11/1992 |
| AU | 653223 B2 | 9/1994 |

(Continued)

OTHER PUBLICATIONS

Andersson, P., et al., "In Vitro Biotransformation of Glucocorticoids in Liver and Skin Homogenate Fraction from Man, Rat and Hairless Mouse," Steroid Biochemistry 16(6):787-795, Pergamon Press, England (Jun. 1982).

(Continued)

*Primary Examiner* — Mark V Stevens
(74) *Attorney, Agent, or Firm* — Sterne, Kessler, Goldstein & Fox P.L.L.C.

(57) ABSTRACT

There is described, inter alia, a coated bead comprising: (a) a granule; (b) a first layer coated over the granule, the first layer comprising a first amount of an active pharmaceutical ingredient comprising a central nervous system stimulant; and (c) a second layer coated over the first layer, the second layer being present in an amount sufficient to substantially delay release of the active pharmaceutical ingredient in the first layer until after the coated bead reaches a distal intestine portion of a subject to whom the coated bead is administered; and (d) the third layer coated over the second layer, the third layer comprising a second amount of the active pharmaceutical ingredient, the third layer being configured to permit substantially immediate release of the active pharmaceutical ingredient comprised therein. Embodiments related to a solid oral pharmaceutical composition are also described.

30 Claims, 7 Drawing Sheets

Related U.S. Application Data continuation of application No. 14/928,276, filed on Oct. 30, 2015, now Pat. No. 9,974,752.

(60) Provisional application No. 62/122,847, filed on Oct. 31, 2014.

(56) References Cited

U.S. PATENT DOCUMENTS

| | | |
|---|---|---|
| 2,772,488 A | 12/1956 | Meltzer |
| 2,791,509 A | 5/1957 | Cosler |
| 3,365,365 A | 1/1968 | Butler et al. |
| 3,370,054 A | 2/1968 | Loew |
| 3,371,015 A | 2/1968 | Sjogren et al. |
| 3,424,842 A | 1/1969 | Eberhard |
| 3,623,997 A | 11/1971 | Powell |
| 3,629,393 A | 12/1971 | Atsushi et al. |
| 3,845,770 A | 11/1974 | Theeuwes et al. |
| 3,870,790 A | 3/1975 | Lowey et al. |
| 3,883,647 A | 5/1975 | Geller |
| 3,901,968 A | 8/1975 | Cohen et al. |
| 3,916,899 A | 11/1975 | Theeuwes et al. |
| 3,927,205 A | 12/1975 | Ohno et al. |
| 3,935,326 A | 1/1976 | Groppenbacher et al. |
| 3,983,233 A | 9/1976 | Brattsand et al. |
| 3,996,356 A | 12/1976 | Grunberg |
| 4,000,254 A | 12/1976 | Gordon et al. |
| 4,060,598 A | 11/1977 | Groppenbacher et al. |
| 4,083,949 A | 4/1978 | Benedikt |
| 4,088,798 A | 5/1978 | Michaelis |
| 4,093,709 A | 6/1978 | Choi et al. |
| 4,140,755 A | 2/1979 | Sheth et al. |
| 4,167,558 A | 9/1979 | Sheth et al. |
| 4,173,626 A | 11/1979 | Dempski et al. |
| 4,182,756 A | 1/1980 | Guzek et al. |
| 4,226,849 A | 10/1980 | Schor |
| 4,234,565 A | 11/1980 | Flodin et al. |
| 4,252,786 A | 2/1981 | Weiss et al. |
| 4,256,108 A | 3/1981 | Theeuwes |
| 4,259,314 A | 3/1981 | Lowey |
| 4,318,400 A | 3/1982 | Peery et al. |
| 4,341,759 A | 7/1982 | Bogentoft et al. |
| 4,357,469 A | 11/1982 | Schor |
| 4,369,172 A | 1/1983 | Schor et al. |
| 4,389,393 A | 6/1983 | Schor et al. |
| 4,439,453 A | 3/1984 | Vogel |
| 4,443,497 A | 4/1984 | Samejima et al. |
| 4,454,108 A | 6/1984 | Iida et al. |
| 4,464,170 A | 8/1984 | Clemens et al. |
| 4,503,031 A | 3/1985 | Glassman |
| 4,520,172 A | 5/1985 | Lehmann et al. |
| 4,526,777 A | 7/1985 | Blume et al. |
| 4,540,566 A | 9/1985 | Davis et al. |
| 4,548,990 A | 10/1985 | Mueller et al. |
| 4,574,080 A | 3/1986 | Roswall et al. |
| 4,592,753 A | 6/1986 | Panoz |
| 4,600,645 A | 7/1986 | Ghebre-Sellassie et al. |
| 4,606,909 A | 8/1986 | Bechgaard et al. |
| 4,606,940 A | 8/1986 | Frank et al. |
| 4,609,542 A | 9/1986 | Panoz et al. |
| 4,610,870 A | 9/1986 | Jain et al. |
| 4,611,008 A | 9/1986 | Heinzelmann |
| 4,634,587 A | 1/1987 | Hsiao |
| 4,666,703 A | 5/1987 | Kopf |
| 4,693,895 A | 9/1987 | Wong et al. |
| 4,695,467 A | 9/1987 | Uemura et al. |
| 4,705,695 A | 11/1987 | Lehmann et al. |
| 4,708,867 A | 11/1987 | Hsiao |
| 4,708,874 A | 11/1987 | De Haan et al. |
| 4,710,519 A | 12/1987 | Finnan et al. |
| 4,716,040 A | 12/1987 | Panoz |
| 4,716,041 A | 12/1987 | Kjornaes et al. |
| 4,721,619 A | 1/1988 | Panoz et al. |
| 4,724,148 A | 2/1988 | Sonobe et al. |
| 4,728,513 A | 3/1988 | Ventouras |
| 4,729,190 A | 3/1988 | Lee |
| 4,740,365 A | 4/1988 | Yukimatsu et al. |
| 4,748,023 A | 5/1988 | Tamas et al. |
| 4,765,988 A | 8/1988 | Sonobe et al. |
| 4,766,012 A | 8/1988 | Valenti |
| 4,770,809 A | 9/1988 | Heidenreich et al. |
| 4,772,475 A | 9/1988 | Fukui et al. |
| 4,783,337 A | 11/1988 | Wong et al. |
| 4,786,503 A | 11/1988 | Edgren et al. |
| 4,786,505 A | 11/1988 | Lovgren et al. |
| 4,786,506 A | 11/1988 | Fontanelli |
| 4,794,001 A | 12/1988 | Mehta et al. |
| 4,798,724 A | 1/1989 | Khanna |
| 4,800,084 A | 1/1989 | Zerbe |
| 4,811,845 A | 3/1989 | Baggett |
| 4,814,178 A | 3/1989 | Bolton et al. |
| 4,816,264 A | 3/1989 | Phillips et al. |
| 4,820,522 A | 4/1989 | Radebaugh et al. |
| 4,826,688 A | 5/1989 | Panoz et al. |
| 4,828,840 A | 5/1989 | Sakamoto et al. |
| 4,837,004 A | 6/1989 | Wu et al. |
| 4,839,177 A | 6/1989 | Colombo et al. |
| 4,842,867 A | 6/1989 | Ayer et al. |
| 4,853,230 A | 8/1989 | Lovgren et al. |
| 4,861,599 A | 8/1989 | Springolo et al. |
| 4,863,744 A | 9/1989 | Urquhart et al. |
| 4,867,984 A | 9/1989 | Patel |
| 4,867,987 A | 9/1989 | Seth |
| 4,880,830 A | 11/1989 | Rhodes |
| 4,889,238 A | 12/1989 | Batchelor |
| 4,891,230 A | 1/1990 | Geoghegan et al. |
| 4,892,739 A | 1/1990 | Shah et al. |
| 4,892,742 A | 1/1990 | Shah |
| 4,894,240 A | 1/1990 | Geoghegan et al. |
| 4,900,557 A | 2/1990 | Dell et al. |
| 4,917,899 A | 4/1990 | Geoghegan et al. |
| 4,931,295 A | 6/1990 | Courtright et al. |
| 4,940,586 A | 7/1990 | Cheng et al. |
| 4,946,685 A | 8/1990 | Edgren et al. |
| 4,950,486 A | 8/1990 | Ayer et al. |
| 4,952,402 A | 8/1990 | Sparks et al. |
| 4,954,350 A | 9/1990 | Jones et al. |
| 4,966,769 A | 10/1990 | Guittard et al. |
| 4,966,770 A | 10/1990 | Giannini et al. |
| 4,968,509 A | 11/1990 | Radebaugh et al. |
| 4,971,805 A | 11/1990 | Kitanishi et al. |
| 4,981,468 A | 1/1991 | Benefiel et al. |
| 4,981,693 A | 1/1991 | Higashi et al. |
| 4,983,401 A | 1/1991 | Eichel et al. |
| 4,983,403 A | 1/1991 | Ardaillon et al. |
| 4,984,592 A | 1/1991 | Hellein |
| 4,994,279 A | 2/1991 | Aoki et al. |
| 5,004,613 A | 4/1991 | Radebaugh et al. |
| 5,008,118 A | 4/1991 | Iwanami et al. |
| 5,011,694 A | 4/1991 | Nuernberg et al. |
| 5,015,479 A | 5/1991 | Mulligan et al. |
| 5,019,397 A | 5/1991 | Wong et al. |
| 5,024,842 A | 6/1991 | Edgren et al. |
| 5,026,560 A | 6/1991 | Makino et al. |
| 5,026,709 A | 6/1991 | Harwood et al. |
| 5,032,406 A | 7/1991 | Dansereau et al. |
| 5,047,007 A | 9/1991 | McNichols et al. |
| 5,047,258 A | 9/1991 | Belanger et al. |
| 5,051,262 A | 9/1991 | Panoz et al. |
| 5,055,306 A | 10/1991 | Barry et al. |
| 5,068,110 A | 11/1991 | Fawzi et al. |
| 5,073,380 A | 12/1991 | Babu et al. |
| 5,084,278 A | 1/1992 | Mehta |
| 5,085,865 A | 2/1992 | Nayak |
| 5,085,866 A | 2/1992 | Cowsar et al. |
| 5,091,175 A | 2/1992 | Imondi et al. |
| 5,093,200 A | 3/1992 | Watanabe et al. |
| 5,095,054 A | 3/1992 | Lay et al. |
| 5,096,717 A | 3/1992 | Wirth et al. |
| 5,112,384 A | 5/1992 | Miura et al. |
| 5,112,621 A | 5/1992 | Stevens et al. |
| 5,128,142 A | 7/1992 | Mulligan et al. |
| 5,130,140 A | 7/1992 | Urban et al. |
| 5,130,171 A | 7/1992 | Prud'Homme et al. |
| 5,133,974 A | 7/1992 | Paradissis et al. |

(56) References Cited

U.S. PATENT DOCUMENTS

| | | |
|---|---|---|
| 5,158,777 A | 10/1992 | Abramowitz et al. |
| 5,160,737 A | 11/1992 | Friedman et al. |
| 5,160,742 A | 11/1992 | Mazer et al. |
| 5,167,964 A | 12/1992 | Muhammad et al. |
| 5,171,580 A | 12/1992 | Iamartino et al. |
| 5,178,866 A | 1/1993 | Wright et al. |
| 5,186,943 A | 2/1993 | Okada et al. |
| 5,198,228 A | 3/1993 | Urban et al. |
| 5,200,193 A | 4/1993 | Radebaugh et al. |
| 5,202,128 A | 4/1993 | Morella et al. |
| 5,202,159 A | 4/1993 | Chen et al. |
| 5,219,621 A | 6/1993 | Geoghegan et al. |
| 5,229,131 A | 7/1993 | Amidon et al. |
| 5,229,134 A | 7/1993 | Mention et al. |
| 5,233,987 A | 8/1993 | Fabian et al. |
| 5,252,341 A | 10/1993 | Sauerbier et al. |
| 5,262,169 A | 11/1993 | Sauerbier et al. |
| 5,266,331 A | 11/1993 | Oshlack et al. |
| 5,273,760 A | 12/1993 | Oshlack et al. |
| 5,275,824 A | 1/1994 | Carli et al. |
| 5,275,825 A | 1/1994 | Okada et al. |
| 5,286,493 A | 2/1994 | Oshlack et al. |
| 5,288,505 A | 2/1994 | Deboeck et al. |
| 5,310,558 A | 5/1994 | Pozzi et al. |
| 5,316,774 A | 5/1994 | Eury et al. |
| 5,320,853 A | 6/1994 | Noda et al. |
| 5,324,717 A | 6/1994 | Berglindh et al. |
| 5,324,718 A | 6/1994 | Loftsson |
| 5,326,570 A | 7/1994 | Rudnic et al. |
| 5,330,766 A | 7/1994 | Morella et al. |
| 5,334,372 A | 8/1994 | Kawamata et al. |
| 5,342,627 A | 8/1994 | Chopra et al. |
| 5,356,467 A | 10/1994 | Oshlack et al. |
| 5,358,718 A | 10/1994 | Sauerbier et al. |
| 5,368,861 A | 11/1994 | Ushimaru et al. |
| 5,370,878 A | 12/1994 | Shah |
| 5,374,430 A | 12/1994 | Newton et al. |
| 5,374,759 A | 12/1994 | Imperante et al. |
| 5,378,474 A | 1/1995 | Morella et al. |
| 5,384,130 A | 1/1995 | Kamada |
| 5,395,626 A | 3/1995 | Kotwal et al. |
| 5,407,687 A | 4/1995 | Coffin et al. |
| 5,439,689 A | 8/1995 | Hendrickson et al. |
| 5,445,829 A | 8/1995 | Paradissis et al. |
| 5,451,409 A | 9/1995 | Rencher et al. |
| 5,472,708 A | 12/1995 | Chen |
| 5,472,711 A | 12/1995 | Baichwal |
| 5,474,786 A | 12/1995 | Kotwal et al. |
| 5,478,573 A | 12/1995 | Eichel et al. |
| 5,489,436 A | 2/1996 | Hoy et al. |
| 5,494,678 A | 2/1996 | Paradissis et al. |
| 5,500,227 A | 3/1996 | Oshlack et al. |
| 5,521,208 A | 5/1996 | York |
| 5,547,878 A | 8/1996 | Kell |
| 5,576,022 A | 11/1996 | Yang et al. |
| 5,580,578 A | 12/1996 | Oshlack et al. |
| 5,597,072 A | 1/1997 | Lieberman et al. |
| 5,639,476 A | 6/1997 | Oshlack et al. |
| 5,643,602 A | 7/1997 | Ulmius |
| 5,652,146 A | 7/1997 | Kell |
| 5,658,590 A | 8/1997 | Heiligenstein et al. |
| 5,661,123 A | 8/1997 | Stalker et al. |
| 5,672,360 A | 9/1997 | Sackler et al. |
| 5,711,967 A | 1/1998 | Juch |
| 5,763,396 A | 6/1998 | Weiner et al. |
| 5,773,031 A | 6/1998 | Shah et al. |
| 5,773,478 A | 6/1998 | Richards et al. |
| 5,785,994 A | 7/1998 | Wong et al. |
| 5,837,284 A | 11/1998 | Mehta et al. |
| 5,840,329 A | 11/1998 | Bai |
| 5,874,090 A | 2/1999 | Baker et al. |
| 5,885,616 A | 3/1999 | Hsiao et al. |
| 5,945,123 A | 8/1999 | Hermelin |
| 6,093,420 A | 7/2000 | Baichwal |
| 6,143,322 A | 11/2000 | Sackler et al. |
| 6,214,379 B1 | 4/2001 | Hermelin |
| 6,228,398 B1 | 5/2001 | Devane et al. |
| 6,255,325 B1 | 7/2001 | Dariani et al. |
| 6,322,819 B1 | 11/2001 | Burnside et al. |
| 6,372,254 B1 | 4/2002 | Ting et al. |
| 6,419,960 B1 | 7/2002 | Krishnamurthy et al. |
| 6,602,887 B2 | 8/2003 | Dariani et al. |
| 6,605,300 B1 | 8/2003 | Burnside et al. |
| 6,627,223 B2 | 9/2003 | Percel et al. |
| 6,632,454 B2 | 10/2003 | Beckert et al. |
| 6,673,367 B1 | 1/2004 | Goldenheim et al. |
| 6,730,325 B2 | 5/2004 | Devane et al. |
| 6,761,904 B2 | 7/2004 | Bertelsen et al. |
| 6,793,936 B2 | 9/2004 | Devane et al. |
| 6,878,387 B1 | 4/2005 | Petereit et al. |
| 6,897,205 B2 | 5/2005 | Beckert et al. |
| 6,902,742 B2 | 6/2005 | Devane et al. |
| 7,048,945 B2 | 5/2006 | Percel et al. |
| 7,070,803 B2 | 7/2006 | Skinhoj et al. |
| 7,083,808 B2 | 8/2006 | Goldenheim et al. |
| 7,195,778 B2 | 3/2007 | Fleshner-Barak et al. |
| 7,247,318 B2 | 7/2007 | Krishnamurthy et al. |
| 7,438,929 B2 | 10/2008 | Beckert et al. |
| 7,438,930 B2 | 10/2008 | Krishnamurthy et al. |
| RE41,148 E | 2/2010 | Burnside et al. |
| RE42,096 E | 2/2011 | Burnside et al. |
| 8,124,653 B2 | 2/2012 | Matalon et al. |
| 8,133,507 B2 | 3/2012 | Yum et al. |
| 8,147,870 B2 | 4/2012 | Yum et al. |
| 8,153,152 B2 | 4/2012 | Yum et al. |
| 8,168,217 B2 | 5/2012 | Yum et al. |
| 8,354,124 B2 | 1/2013 | Yum et al. |
| 8,420,120 B2 | 4/2013 | Yum et al. |
| 8,580,310 B2 | 11/2013 | Krishnamurthy et al. |
| 8,846,100 B2 | 9/2014 | Shojaei et al. |
| 8,911,777 B2 | 12/2014 | Coulter |
| 8,945,614 B2 | 2/2015 | Yum et al. |
| 8,951,556 B2 | 2/2015 | Yum et al. |
| 8,974,821 B2 | 3/2015 | Yum et al. |
| 9,066,869 B2 | 6/2015 | Krishnamurthy et al. |
| 9,107,804 B2 | 8/2015 | Rubino et al. |
| 9,161,918 B2 | 10/2015 | Venkatesh |
| 9,161,919 B2 | 10/2015 | Venkatesh |
| 9,233,160 B2 | 1/2016 | Yum et al. |
| 9,364,430 B2 | 6/2016 | Babul |
| 9,517,271 B2 | 12/2016 | Yum et al. |
| 9,522,119 B2 | 12/2016 | Odidi |
| 9,566,249 B2 | 2/2017 | Venkatesh |
| 9,579,293 B2 | 2/2017 | Venkatesh |
| 9,700,515 B2 | 7/2017 | Odidi |
| 9,700,516 B2 | 7/2017 | Odidi |
| 9,801,823 B2 | 10/2017 | Krishnamurthy et al. |
| 9,801,939 B2 | 10/2017 | Odidi |
| 9,884,022 B2 | 2/2018 | Deshmukh et al. |
| 10,111,839 B2 * | 10/2018 | Vargas Rincon .... A61K 9/5078 |
| 10,292,939 B2 * | 5/2019 | Vargas Rincon .... A61K 9/5078 |
| 2001/0012847 A1 | 8/2001 | Lam et al. |
| 2001/0055613 A1 | 12/2001 | Burnside et al. |
| 2002/0034544 A1 | 3/2002 | Skinhoj et al. |
| 2002/0054907 A1 | 5/2002 | Devane et al. |
| 2002/0147232 A1 | 10/2002 | Sundgreen et al. |
| 2002/0192282 A1 | 12/2002 | Beckert et al. |
| 2002/0193445 A1 | 12/2002 | Bertelsen et al. |
| 2003/0054033 A1 | 3/2003 | Krishnamurthy et al. |
| 2003/0124188 A1 | 7/2003 | Burnside et al. |
| 2003/0129229 A1 | 7/2003 | Krsek |
| 2003/0129237 A1 | 7/2003 | Devane et al. |
| 2003/0153607 A1 | 8/2003 | Glinecke et al. |
| 2003/0170304 A1 | 9/2003 | Devane et al. |
| 2004/0091531 A1 | 5/2004 | Glinecke et al. |
| 2004/0091532 A1 | 5/2004 | Mehta |
| 2004/0131680 A1 | 7/2004 | Goldenheim et al. |
| 2004/0161382 A1 | 8/2004 | Yum et al. |
| 2004/0197405 A1 | 10/2004 | Devane et al. |
| 2004/0219213 A1 | 11/2004 | Burnside et al. |
| 2004/0228802 A1 | 11/2004 | Chang et al. |
| 2005/0089571 A1 | 4/2005 | Beckert et al. |
| 2005/0136111 A1 | 6/2005 | Glinecke et al. |
| 2006/0046008 A1 | 3/2006 | Wildfang |

(56) References Cited

U.S. PATENT DOCUMENTS

| | | |
|---|---|---|
| 2006/0159757 A1 | 7/2006 | Payne |
| 2006/0204576 A1 | 9/2006 | Petereit et al. |
| 2006/0240105 A1 | 10/2006 | Devane et al. |
| 2007/0104789 A1 | 5/2007 | Spector |
| 2007/0264323 A1 | 11/2007 | Shojaei et al. |
| 2007/0264325 A1 | 11/2007 | Krishnamurthy et al. |
| 2007/0281023 A1 | 12/2007 | Glinecke et al. |
| 2008/0069872 A1 | 3/2008 | Rubio Badia et al. |
| 2008/0118556 A1 | 5/2008 | Devane et al. |
| 2008/0193522 A1 | 8/2008 | Meier et al. |
| 2008/0206321 A1 | 8/2008 | Yum et al. |
| 2008/0206324 A1 | 8/2008 | Gryczke et al. |
| 2009/0023689 A1 | 1/2009 | Yum et al. |
| 2009/0023690 A1 | 1/2009 | Yum et al. |
| 2009/0123554 A1 | 5/2009 | Krishnamurthy et al. |
| 2009/0280176 A1 | 11/2009 | Vieira et al. |
| 2009/0297597 A1 | 12/2009 | Liversidge et al. |
| 2009/0297602 A1 | 12/2009 | Devane et al. |
| 2009/0324716 A1 | 12/2009 | Shen et al. |
| 2010/0136106 A1 | 6/2010 | Liversidge et al. |
| 2010/0151010 A1 | 6/2010 | Petereit et al. |
| 2010/0151020 A1 | 6/2010 | Rosenberger et al. |
| 2010/0226978 A1 | 9/2010 | Petereit et al. |
| 2010/0260844 A1 | 10/2010 | Scicinski et al. |
| 2010/0297221 A1 | 11/2010 | Coulter |
| 2010/0316712 A1 | 12/2010 | Nangia et al. |
| 2011/0064803 A1 | 3/2011 | Devane et al. |
| 2011/0212175 A1 | 9/2011 | Kim et al. |
| 2011/0262496 A1 | 10/2011 | Desai |
| 2011/0268799 A1 | 11/2011 | Dixit et al. |
| 2012/0015007 A1 | 1/2012 | Bredenberg et al. |
| 2012/0065221 A1 | 3/2012 | Babul |
| 2012/0128771 A1 | 5/2012 | Venkatesh |
| 2012/0135072 A1 | 5/2012 | Yum et al. |
| 2012/0135073 A1 | 5/2012 | Yum et al. |
| 2012/0178771 A1 | 7/2012 | Babul et al. |
| 2013/0022654 A1 | 1/2013 | Deshmukh et al. |
| 2013/0236554 A1 | 9/2013 | Tengler |
| 2013/0287845 A1 | 10/2013 | Yum et al. |
| 2013/0295168 A1 | 11/2013 | Yum et al. |
| 2014/0099361 A1 | 4/2014 | Krishnamurthy et al. |
| 2014/0120185 A1 | 5/2014 | Hirose et al. |
| 2014/0200237 A1 | 7/2014 | Babul |
| 2014/0212483 A1 | 7/2014 | Lickrish et al. |
| 2014/0255594 A1 | 9/2014 | Rubino et al. |
| 2015/0196644 A1 | 7/2015 | Yum et al. |
| 2015/0313850 A1 | 11/2015 | Krishnamurthy et al. |
| 2016/0193345 A1 | 7/2016 | Yum et al. |
| 2016/0215069 A1 | 7/2016 | Stern et al. |
| 2016/0220491 A1 | 8/2016 | Rubino et al. |
| 2017/0000783 A1 | 1/2017 | Devane et al. |
| 2017/0071926 A1 | 3/2017 | Krishnamurthy et al. |
| 2017/0079921 A1 | 3/2017 | Krishnamurthy et al. |
| 2017/0112774 A1 | 4/2017 | Venkatesh |
| 2017/0135999 A1 | 5/2017 | Krishnamurthy et al. |
| 2017/0165255 A1 | 6/2017 | Yum et al. |
| 2017/0258912 A1 | 9/2017 | Odidi |

FOREIGN PATENT DOCUMENTS

| | | |
|---|---|---|
| CA | 1183665 A | 3/1985 |
| CA | 1297368 C | 3/1992 |
| CA | 2 348 090 A1 | 4/2000 |
| CA | 2 355 644 A1 | 6/2000 |
| CA | 2 368 367 A1 | 10/2000 |
| CA | 2 373 909 A1 | 9/2001 |
| CA | 2 426 883 A1 | 5/2002 |
| CA | 2 502 371 A1 | 5/2004 |
| CA | 2507631 A1 | 6/2004 |
| CA | 2 537 103 A1 | 5/2005 |
| CA | 2 566 497 A1 | 12/2005 |
| CA | 2 683 409 A1 | 10/2008 |
| CA | 2 754 604 A1 | 9/2010 |
| CA | 2 830 788 A1 | 9/2012 |
| CA | 2 877 190 A1 | 1/2014 |
| CA | 2 926 082 A1 | 4/2015 |
| CA | 2 933 587 A1 | 6/2015 |
| EP | 0054010 A1 | 6/1982 |
| EP | 0040590 A3 | 1/1983 |
| EP | 0074584 A2 | 3/1983 |
| EP | 0122077 A2 | 10/1984 |
| EP | 0232690 A1 | 8/1987 |
| EP | 0239361 A1 | 9/1987 |
| EP | 0248548 A2 | 12/1987 |
| EP | 0278174 A2 | 8/1988 |
| EP | 0325086 A2 | 7/1989 |
| EP | 0325843 A2 | 8/1989 |
| EP | 0327295 A2 | 8/1989 |
| EP | 0377517 A3 | 10/1990 |
| EP | 0250374 B1 | 5/1991 |
| EP | 0463877 A1 | 1/1992 |
| EP | 0514814 A1 | 11/1992 |
| EP | 0631781 A1 | 1/1995 |
| GB | 377518 A | 7/1932 |
| GB | 1182124 A | 2/1970 |
| GB | 1245467 A | 9/1971 |
| GB | 2098867 A | 12/1982 |
| GB | 2141342 A | 12/1984 |
| GB | 2159715 A | 12/1985 |
| GB | 2178313 A | 2/1987 |
| GB | 2209280 A | 5/1989 |
| GB | 2253348 A | 9/1992 |
| JP | S55149211 A | 11/1980 |
| JP | H01165518 A | 6/1989 |
| JP | H0291028 A | 3/1990 |
| JP | 2000516610 A | 12/2000 |
| JP | 2016006608 A | 1/2016 |
| WO | WO-8300435 A1 | 2/1983 |
| WO | WO-8500481 A1 | 1/1985 |
| WO | WO-8603676 A1 | 7/1986 |
| WO | WO-8908448 A1 | 9/1989 |
| WO | WO-9221333 A3 | 1/1993 |
| WO | WO-9317673 A1 | 9/1993 |
| WO | WO-9703671 A1 | 2/1997 |
| WO | WO-9703672 A1 | 2/1997 |
| WO | WO-9703673 A1 | 2/1997 |
| WO | WO-9806380 A2 | 2/1998 |
| WO | WO-9814168 A2 | 4/1998 |
| WO | WO-9818454 A1 | 5/1998 |
| WO | WO-9823263 A1 | 6/1998 |
| WO | WO-9848782 A1 | 11/1998 |
| WO | WO-9908662 | 2/1999 |
| WO | WO-9908662 | 2/1999 |
| WO | WO-9962496 A1 | 12/1999 |
| WO | WO-0023055 A1 | 4/2000 |
| WO | WO-0025752 A1 | 5/2000 |
| WO | WO-0028990 A1 | 5/2000 |
| WO | WO-0035426 A2 | 6/2000 |
| WO | WO-0035450 A1 | 6/2000 |
| WO | WO-0168058 A1 | 9/2001 |
| WO | WO-0174334 A1 | 10/2001 |
| WO | WO-0174335 A1 | 10/2001 |
| WO | WO-0188092 A2 | 11/2001 |
| WO | WO-0189473 A1 | 11/2001 |
| WO | WO-0235426 A1 | 5/2002 |
| WO | WO-03000032 A1 | 1/2003 |
| WO | WO-2003080032 | 10/2003 |
| WO | WO-2004054542 A2 | 7/2004 |
| WO | WO-2006078811 A2 | 7/2006 |
| WO | WO-2006132752 A1 | 12/2006 |
| WO | WO-2007011473 A1 | 1/2007 |
| WO | WO-2007037790 A2 | 4/2007 |
| WO | WO-2007070082 A1 | 6/2007 |
| WO | WO-2007093642 A2 | 8/2007 |
| WO | WO-2008079102 A1 | 7/2008 |
| WO | WO-2008083442 A1 | 7/2008 |
| WO | WO-2012080834 A1 | 6/2012 |

(56) References Cited

FOREIGN PATENT DOCUMENTS

| | | |
|---|---|---|
| WO | WO-2014174387 A1 | 10/2014 |
| WO | WO 2015/188092 A1 | 12/2015 |

OTHER PUBLICATIONS

Aoyama, T., et al., "Pharmacokinetics and Pharmacodynamics of (+)-Threo-Methylphenidate Enantiomer in Patients With Hypersomnia," Clinical Pharmacology and Therapeutics 55(3):270-276, Hoboken, NJ : Wiley, United States (Mar. 1994).
Aqua coat (Ethylcellulose ), pp. 17-36, 1985, Manufacturer's Info.
Aquacoat, Ethylcellulose, 1987, Manufacturer's Info.
Ariens, E.J, "Racemic Therapeutics-Ethical and Regulatory Aspects," European Journal of Clinical Pharmacology 41(2):89-93, New York, Springer, Germany (1991).
Ariens, E.J, "Stereoselectivity in Pharmacodynamics and Pharmacokinetics," Swiss Medical Weekly 120(5):131-134, EMH Swiss Medical Publishers, Switzerland (Feb. 1990).
Biederman, J., et al., "A Double-Blind Placebo Controlled Study of Desipramine in the Treatment of ADD: I. Efficacy," American Academy of Child and Adolescent Psychiatry 28(5):777-784, New York : Elsevier, United States (Sep. 1989).
Biederman, J., et al., "Comorbidity of Attention Deficit Hyperactivity Disorder with Conduct, Depressive, Anxiety, and Other Disorders," American Journal of Psychiatry 148(5):564-577, American Psychiatric Association, United States (May 1991).
Biederman, J., et al., "Patterns of Psychiatric Comorbidity, Cognition, and Psychosocial Functioning in Adults with Attention Deficit Hyperactivity Disorder," American Journal of Psychiatry 150(12):1792-1798, American Psychiatric Association, United States (Dec. 1993).
Birmaher, B., et al., "Sustained Release Methylphenidate: Pharmacokinetic Studies in Addh Males," American Academy of Child and Adolescent Psychiatry 28(5):768-772, New York : Elsevier, United States (Sep. 1989).
Castle, W.E., et al., "Linkage Studies of the Rat (*Rattus norvegicus*)," Proceedings of the National Academy of Sciences 27(8):394-398, National Academy of Sciences, United States (Aug. 1941).
Catapres (Cionidine). Physicians' Desk Reference, 48th Edition. ed. Montvale, NJ: Thomson Healthcare, 1994, pp. 612-614.
Child, A.H., et al., "Joint Hypermobility Syndrome: Inherited Disorder of Collagen Synthesis," Rheumatology 13(2):239-243, Journal of Rheumatology Publishing Co, Canada (1986).
Chouinard, G., et al., "An Early Phase II Clinical Trial of Tomoxetine (LY139603) in the Treatment of Newly Admitted Depressed Patients," Psychopharmacology (Berl) 83(1):126-128, New York, Springer-Verlag, Germany (1984).
Chouinard, G., et al., "An Early Phase II Clinical Trial with Followup of Tomoxetine (LY139603) in the Treatment of Newly Admitted Depressed Patients," Psychopharmacology Bulletin 21(1):73-76, Redondo Beach, CA : MedWorks Media, United States (1985).
Chumpradit, S., et al., "Iodinated Tomoxetine Derivatives as Selective Ligands for Serotonin and Norepinephrine Uptake Sites," Medicinal Chemistry 35(23):4492-4497, Washington DC : American Chemical Society, United States (Nov. 1992).
Corrigan, O.I., et al., "The Biopharmaceutic Drug Classification and Drugs Administered in Extended Release (ER) Formulations," Advances in Experimental Medicine and Biology 423:111-128, Kluwer Academic/Plenum Publishers, United States (1997).
Covera-HS, Physicians' Desk Reference. 51st Edition, Montvale, NJ: Thomson Healthcare, 1997, pp. 2573-2576.
Cusack, B., et al., "Binding of Antidepressants to Human Brain Receptors: Focus on Newer Generation Compounds," Psychopharmacology 114(4):559-565, Springer-Verlag, Germany (May 1994).
Danielsson, A., et al., "A Controlled Randomized Trial of Budesonide Versus Prednisolone Retention Enemas In Active Distal Ulcerative Colitis," Scandinavian Journal of Gastroenterology 22(8):987-992, Informa Healthcare, England (Oct. 1987).

De Haan, P., et al., "Oral Controlled Release Dosage Forms. A Review," Pharmaceutisch Weekblad 6(2):57-67, Bohn, Scheltema En Holkema, Netherlands (Apr. 1984).
De Scalzi, M., et al., "Circadian Rhythms of Arterial Blood Pressure," Chronobiologia 13(3):239-244, Associated Chronobiologia Researchers, Italy (Jul.-Sep. 1986).
Depakote Tablets, Physicians' Desk Reference. 51st Edition, Montvale, NJ: Thomson Healthcare, 1997, pp. 418-422.
Drimmer, E.J., et al., "Desipramine and Methylphenidate Combination Treatment for Depression: Case Report," American Journal of Psychiatry 140(2):241-242, American Psychiatric Association, United States (Feb. 1983).
Eckerman, D.A., et al., "Enantioselective Behavioral Effects of Threo-Methylphenidate in Rats," Pharmacology Biochemistry and Behavio 40(4):875-880, NY : Elsevier, United States (Dec. 1991).
Elavil (Amitriptyline), Physicians' Desk Reference, 47th Edition, Montvale, NJ: Thomson Healthcare, 1993, pp. 2372-2374.
Erramouspe, J., et al., "Effect on Dissolution from Halving Methylphenidate Extended-Release Tablets," Annals of Phannacotherapy 31(10):1123-1126, Thousand Oaks, CA : Sage, United States (Oct. 1997).
Farid, N. A., et al., "Single-Dose and Steady-State Pharmacokinetics of Tomoxetine in Normal Subjects," Clinical Pharmacology 25(4):296-301, Oxford : Wiley, England (May-Jun. 1985).
Fuller, R.W., et al., "Antagonism by Tomoxetine of the Depletion of Norepinephrine and Epinephrine in Rat Brain by Alpha-Methyl-M-Tyrosine," Research Communications in Chemical Pathology and Pharmacology 41(1):169-172, P. J. D. Publications, United States (Jul. 1983) ).
Fuller, R.W., et al., "Effects of Duloxetine, an Antidepressant Drug Candidate, on Concentrations of Monoamines and Their Metabolites in Rats and Mice," Journal of Pharmacology and Experimental Therapeutics 269(1):132-136, American Society for Pharmacology and Experimental Therapeutics, United States (Apr. 1994).
Fuller, R.W., et al., "Serotonin Reuptake Blockers in Vitro and in Vivo," Clinical Psychopharmacology 7(6 Suppl):36S-43S, Williams and Wilkins, United States (Dec. 1987).
Gamstedt, A., et al., "Effect of Betamethasone Treatment on Iodothyronines and Thyroid Hormone-Binding Proteins During controlled nutrition. A study on patients with chronic inflammatory bowel disease," Acta Endocrinol (Copenh) 103(2):188-191, Periodica, Denmark (Jun. 1983).
Gehlert, D.R., et al., "Localization of Rat Brain Binding Sites for [3H]Tomoxetine, an Enantiomerically Pure Ligand for Norepinephrine Reuptake Sites," Neuroscience Letters 157(2):203-206, Elsevier Scientific Publishers Ireland, Ireland (Jul. 1993) ).
Gilman, V., et al., "The Top Pharmaceuticals that Changed the World: Ritalin," Chemical & Engineering News 83:25, (2005).
Green, W.H., et al., "Nonstimulant Drugs in the Treatment of Attention Deficit Hyperactivity Disorder," Child and adolescent psychiatric clinics of North America 1:449-465, (1992).
Grob, C.S., et al., "Suspected Adverse Methylphenidate-Imipramine Interactions in Children," Developmental & Behavioral Pediatrics 7(4):265-267, Lippincott Williams & Wilkins, United States (Aug. 1986).
Heile, B, "Critical Factors Influencing Gastrointestinal Absorption-What is the Role of Pellets?," Acta Pharmaceutica Technologica 28 (2):149-157, (1982).
International Search Report and Written Opinion for Application No. PCT/US2015/34466 dated Aug. 26, 2015.
Jewell D.P, "Corticosteroids for the Management of Ulcerative Colitis and Crohn's Disease," Gastroenterology Clinics of North America 18(1):21-34, Elsevier Health Science Division, United States (Mar. 1989).
Johanson, C.E., et al., "The Discriminative Stimulus Effects of Cocaine in Pigeons," Pharmacology and Experimental Therapeutics 267(1):1-8, American Society for Pharmacology and Experimental Therapeutics, United States (Oct. 1993).
Johans Son, S.A., et al., "Topical and Systemic Glucocorticoid Potencies of Budesonide, Beclomethasone Dipropionate and Prednisolone in Man," European journal of respiratory diseases. Supplement 122:74-82, Munksgaard International Publishers, Denmark (1982).

(56) References Cited

OTHER PUBLICATIONS

Kapseals Dilantin, Physicians' Desk Reference. 51st Edition, Montvale, NJ: Thomson Healthcare, 1997, pp. 1965-1970.
Keshavarzian, A., et al., "MPTP-Induced Duodenal Ulcers in Rat. Prevention by Reuptake Blockers for Serotonin and Norepinephrine, but Not Dopamine," Gastroenterology 98(3):554-560, W.B. Saunders, United States (1990).
Khutoryanskiy, V.V., "Supramolecular Materials: Longer and Safer Gastric Residence," Nature Materials 14(10): 963-964, London, Nature Pub. Group, United Kingdom (2015).
Krasznai, A., et al., "Decreased Number of Steroid Receptors of Circulating Lymphocytes in Crohn's Disease and Ulcerative Colitis," Haematologia (Budapest) 19(4):299-301, Utrecht : Vsp, Netherlands (1986).
Kumana, C.R., et al., "Beclomethasone Dipropionate Enemas for Treating Inflammatory Bowel Disease without Producing Cushing's Syndrome or Hypothalamic Pituitary Adrenal Suppression," Lancet 1(8272):579-583, London : Elsevier, England (Mar. 1982).
Lehmann., et al., Practical Course in Lacquer Coating. N. p.: K. Lehmann, 1989.
Levine, D.S., et al., "Coating of Oral Beclomethasone Dipropionate Capsules with Cellulose Acetate Phthalate Enhances Delivery of Topically Active Antiinflammatory Drug to the Terminal Ileum," Gastroenterology 92(4):1037-1044, W.B. Saunders, United States (Apr. 1987).
Licamele, W.L., et al., "The Concurrent Use of Lithium and Methylphenidate in a Child," American Academy of Child and Adolescent Psychiatry 28(5):785-787, New York : Elsevier, United States (Sep. 1989).
Ismo, Physicians' Desk Reference, 51st Edition, Montvale, NJ: Thomson Healthcare, 1997, pp. 2844-2845.
Malchow, H., et al., "Therapy of Crohn's disease," Deutsche Medizinische Wochenschrift 109(47):1811-1816, Thieme, Germany (Nov. 1984).
Manley, R.H., et al., "Binary Solvents for Zein," Industrial & Engineering Chemistry 35(6):661-665, (1943).
McGinity, Aqueous Polymeric Coatings for Pharmaceutical Dosage Forms, Second Edition, pp. 124-125, 272-273, 280-285.
Medical Economics Company. "Anafranil (Clomipramine)" Physicians' Desk Reference. 47th Edition, Montvale, NJ: Thomson Healthcare, 1993, pp. 671-675.
Munday, D.L., et al., "Changes in Drug Release Rate: Effect of Stress Storage Conditions on Film Coated Mini-Tablets," Drug Development and Industrial Pharmacy 17(15):2135-2143, (1991).
Norpramin (Desipramine), Physicians' Desk Reference. 47th Edition, Montvale, NJ: Thomson Healthcare, 1993, pp. 1389-1390.
Oberlender, R., et al., "Tomoxetine and the Stereo selectivity of Drug Action," Pharmacy and Pharmacology 39(12):1055-1066, Pharmaceutical Society of Great Britain, England (Dec. 1987).
Pamelor (Nortriptyline), Physicians' Desk Reference. 47th Edition, Montvale, NJ: Thomson Healthcare, 1993, pp. 2115-2116.
Patrick, K.S., et al., "Pharmacology of the Enantiomers of Threo-Methylphenidate," Journal of Pharmacology and Experimental Therapeutics 241(1):152-158, American Society for Pharmacology and Experimental Therapeutics, United States (Apr. 1987).
Patrick, K.S., et al., "The Absorption of Sustained-Release Methylphenidate Formulations Compared to an Immediate-Release Formulation," Biopharmaceutics & Drug Disposition 10(2):165-171, Wiley, England (Mar.-Apr. 1989).
Pelham, W.E., et al., "Relative Efficacy of Long-Acting Stimulants on Children with Attention Deficit-Hyperactivity Disorder: A Comparison of Standard Methylphenidate, Sustained-Release Methylphenidate, Sustained-Release Dextroamphetamine, and Pemoline," Pediatrics 86(2):226-237, American Academy of Pediatrics, United States (Aug. 1990).
Product Monograph Biphentin, prepared on Mar. 8, 2006, and revised on Jul. 27, 2007.
Prozac (Fiuoxetine), Physicians' Desk Reference, 48th Edition, Montvale, NJ: Thomson Healthcare, 1994, pp. 877-880.
Purdue Pharma. "Biphentin" ,package insert, Pickering, ON, 2012.

Quinn, D., et al., "Single-Dose Pharmacokinetics of Multilayer-Release Methylphenidate and Immediate-Release Methylphenidate in Children with Attention-Deficit/Hyperactivity Disorder, " Clinical Pharmacology 47(6):760-766, Wiley, England, (Jun. 2007).
Rapport, M.D., et al., "Methylphenidate and Desipramine in Hospitalized Children: i. Separate and Combined Effects on Cognitive Function," American Academy of Child and Adolescent Psychiatry 32(2):333-342, New York : Elsevier, United States (Mar. 1993).
Remington: The Science and Practice of Pharmacy, pp. 1592, 1980.
Ritalin S.R. Physicians' Desk Reference. 46th Edition, Montvale, NJ: Thomson Healthcare, 1992, pp. 880-881.
Ryan, N.D, "Heterocyclic Antidepressants in Children and Adolescents," Child and Adolescent Psychopharmacology 1(1):21-31, (1990).
Sinemet, Physicians' Desk Reference, 51st Edition, 1997, pp. 959-963.
Spencer, T., et al., "Nortriptyline Treatment of Children with Attention-Deficit Hyperactivity Disorder and Tic Disorder or Tourette's Syndrome," American Academy of Child and Adolescent Psychiatry 32(1):205-210, New York : Elsevier, United States (Jan. 1993).
Springer, J.P., et al., "Facilitatory and Inhibitory Effects of Selective Norepinephrine Reuptake Inhibitors on Hypogastric Nerve-Evoked Urethral Contractions in the Cat: A Prominent Role of Urethral Beta-Adrenergic Receptors," Journal of Urology 152(2 Pt 1):515-519, New York : Elsevier, United States (Aug. 1994).
Steele, M., et al., "A Randomized, Controlled Effectiveness Trial of OROS-Methylphenidate Compared to Usual Care with Immediate-Release Methylphenidate in Attention Deficit-Hyperactivity Disorder," Clinical Pharmacology 13(1): e50-e62, Pulsus Group [for the] Canadian Society for Clinical Pharmacology, (Winter 2006).
Einberg, S., et al., "A Case of Mania Associated with Tomoxetine," American Journal of Psychiatry 142(12):1517-1518, (Dec. 1985).
Swallen, L.C., et al., "Zein. A new industrial protein," Industrial and Engineering Chemistry 33(3):394-397, (1941).
Swanson, J.M., et al., "The Use of a Laboratory School Protocol to Evaluate Concepts about Efficacy and Side Effects of New Formulations of Stimulant Medications," Attention Disorders 6 Suppl 1:S73-S88, Thousand Oaks : SAGE Publications, United States (2002).
Ferry, P., et al., "Pharmacological Characterization of the Novel Discriminative Stimulus Effects of a Low Dose of Cocaine," Pharmacology and Experimental Therapeutics 270(3):1041-1048, American Society for Pharmacology and Experimental Therapeutics, United States (Sep. 1994).
Thomas, P., et al., "Absorption of Delayed-Release Prednisolone in Ulcerative Colitis and Crohn's Disease," Pharmacy and Pharmacology 37(10):757-758, Wiley, England (Oct. 1985).
Thorazine (Chlorpromazine), Physicians' Desk Reference. 47th Edition, Montvale, NJ: Thomson Healthcare, 1993. pp. 2327-2330.
Tofranil (Imipramine), Physicians' Desk Reference. 47th Edition, Montvale, NJ: Thomson Healthcare, 1993, pp. 1070-1074.
Tyndale, R.F., et al., "Neuronal Cytochrome P45011D1 (debrisoquinelsparteine-Type): Potent Inhibition of Activity by (-)-Cocaine and Nucleotide Sequence Identity to Human Hepatic P450 Gene CYP2D6," Molecular pharmacology 40(1):63-68, American Society for Pharmacology and Experimental Therapeutics, United States (Jul. 1991).
United States Pharmacopeia Convention. "<2040> Disintegration and Dissolution of Nutritional Supplements." United States Pharmacopeia I National Formulary. USP231NF18 vol. Rockville, MD: United States Pharmacopeia! Convention, Inc., 1995. 2184-5, 2577-8, 2833-4, 3794-5.
United States Pharmacopeia Convention. "<711> Dissolution." United States Pharmacopeia I National Formulary. USP231NF18 vol. Rockville, MD: United States Pharmacopeia Convention, Inc., 1995. 1791-4, 2185, 2577-8, 2833-4, 3208-9, 3794-5.
United States Pharmacopeia Convention. "<724> Drug Release." United States Pharmacopeia I National Formulary. USP231NF18 vol. Rockville, MD: United States Pharmacopeia! Convention, Inc., 1995. 1793-9, 2534-6, 2709-15, 3012-7, 3209-15, 3468-74.
Vitiello, B., et al., "Methylphenidate Dosage for Children with ADHD Over Time Under Controlled Conditions: Lessons From the MTA," American Academy of Child and Adolescent Psychiatry 40(2):188-196, New York : Elsevier, United States (Feb. 2001).

(56) References Cited

OTHER PUBLICATIONS

Wellbutrin (Bupropion), Physicians' Desk Reference, 47th Edition, Montvale, NJ: Thomson Healthcare, 1993, pp. 842-844.
Wilens, T.E., et al., "Nortriptyline in the Treatment of Adhd: A Chart Review of 58 Cases," American Academy of Child & Adolescent Psychiatry 32(2):343-349, New York : Elsevier, United States (Mar. 1993).
Wolman, S.L., et al., "Use of Oral Budesonide in a Patient with Small Bowel Crohn's Disease and Previous Pseudotumor Cerebri Secondary to Steroids," Scandinavian Journal of Gastroenterology 24 Suppl 158:146-147, (1989).
Wong, D.T., et al., "A New Inhibitor of Norepinephrine Uptake Devoid of Affinity for Receptors in Rat Brain," Pharmacology and Experimental Therapeutics 222(1):61-65, Williams & Wilkins, United States (Jul. 1982).
Wong, D.T., et al., "LY248686, a New Inhibitor of Serotonin and Norepinephrine Uptake," Neuropsychopharmacology 8(1):23-33, London : Nature Publishing Group, England (Jan. 1993).
Wong, D.T., et al., "The Comparison of Fluoxetine and Nisoxetine with Tricyclic Antidepressants in Blocking the Neurotoxicity of P-Chloroamphetamine and 6-Hydroxydopamine in the Rat Brain," Research Communications in Chemical Pathology and Pharmacology 15(2):221-231, P. J. D. Publications, United States (Oct. 1976).
Zerbe, R.L., et al., "Clinical Pharmacology of Tomoxetine, a Potential Antidepressant," Pharmacology and Experimental Therapeutics 232(1):139-143, American Society for Pharmacology and Experimental Therapeutics, United States (Jan. 1985).
Zhang, L., et al., "Imipramine as a Discriminative Stimulus," Pharmacology and Experimental Therapeutics 259(3):1088-1093, American Society for Pharmacology and Experimental Therapeutics, United States (Dec. 1991).
*Rhodes Pharmaceuticals L.P.* vs. *Actavis, Inc., Actavis Elizabeth LLC, Actavis LLC, and Allergan PLC*, Defendants' Preliminary Invalidity Contentions for U.S. Pat. Nos. 6,419,960, 7,083,808, 7,438,930, 7,247,318, 8,580,310, and 9,066,869, Civil Action No. 16/1668 (WHW)(CLW), Oct. 7, 2016. 229 pages.
Malchow, H., et al., "Therapy of Crohn's disease," Deutsche Medizinische Wochenschrift 109(47):1811-1816, Thieme, Germany (Nov. 1984). (English Translation).
Office Action dated Oct. 11, 2018, in U.S. Appl. No. 16/120,999, Vargas Rincon et. al., filed Sep. 4, 2018, 18 pages.
Office Action dated Dec. 4, 2018, in U.S. Appl. No. 16/120,900, Vargas Rincon et. al., filed Sep. 4, 2018, 7 pages.
Office Action dated Mar. 22, 2017, in U.S. Appl. No. 14/928,276, Vargas Rincon et. al., filed Oct. 30, 2015, 13 pages.
Office Action dated Oct. 16, 2017, in U.S. Appl. No. 14/928,276, Vargas Rincon et. al., filed Oct. 30, 2015, 24 pages.
Coghill, D., et al., "Long-acting methylphenidate formulations in the treatment of attention-deficit/hyperactivity disorder: a systematic review of head-to-head studies," BMC Psychiatry 13: 1-24, Springer Nature, United Kingdom (2013).
Office Action dated Feb. 1, 2019, in U.S. Appl. No. 16/185,730, Vargas Rincon et al., filed Nov. 9, 2018, 13 pages.
Office Action dated Apr. 4, 2019, in U.S. Appl. No. 16/282,858, Vargas Rincon et al., filed Feb. 22, 2019, 10 pages.
Office Action dated Apr. 4, 2019, in U.S. Appl. No. 16/282,876, Vargas Rincon et al., filed Feb. 22, 2019, 8 pages.
Office Action dated Jun. 14, 2019, in U.S. Appl. No. 16/399,574, Vargas Rincon et al., filed Apr. 30, 2019, 12 pages.
Office Action dated Jun. 13, 2019, in U.S. Appl. No. 16/195,418, Donnelly, G., et al., filed Nov. 19, 2018, 7 pages.
Office Action dated Jul. 22, 2019, in U.S. Appl. No. 16/422,177, inventor Vargas Rincon, R.A., et al., filed May 24, 2019, 14 pages.
Office Action dated Aug. 19, 2019, in U.S. Appl. No. 16/399,571, inventor Vargas Rincon, R.A., et al., filed Apr. 30, 2019, 18 pages.

\* cited by examiner

Figure 1: Results of PK Study 063-001
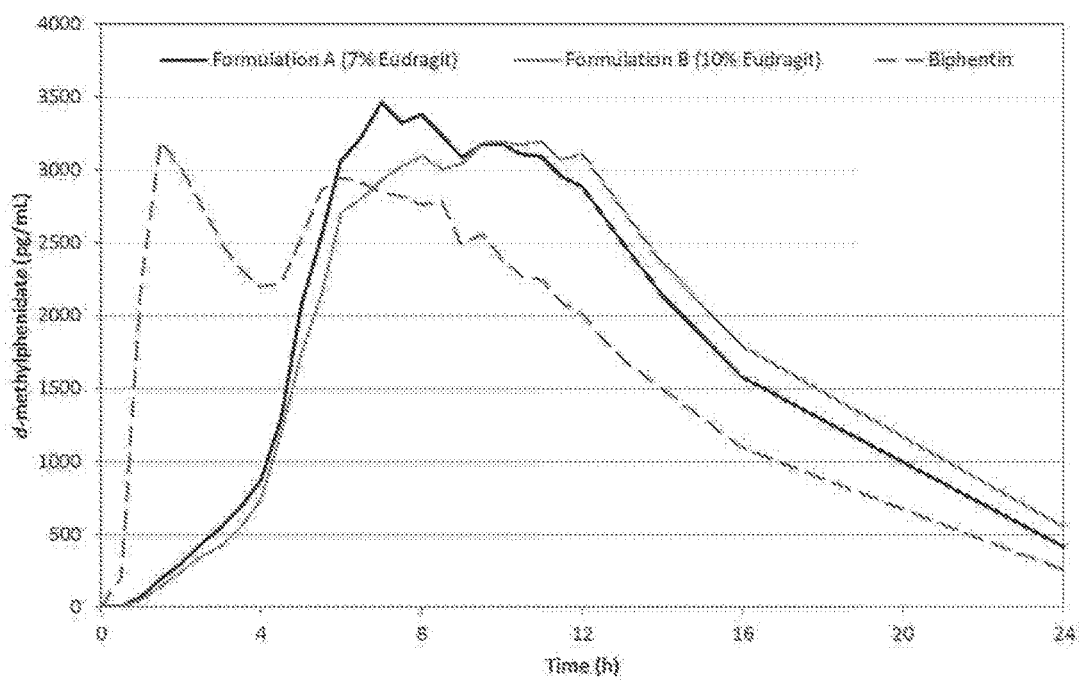
Figure 2: Results of PK Study 063-002
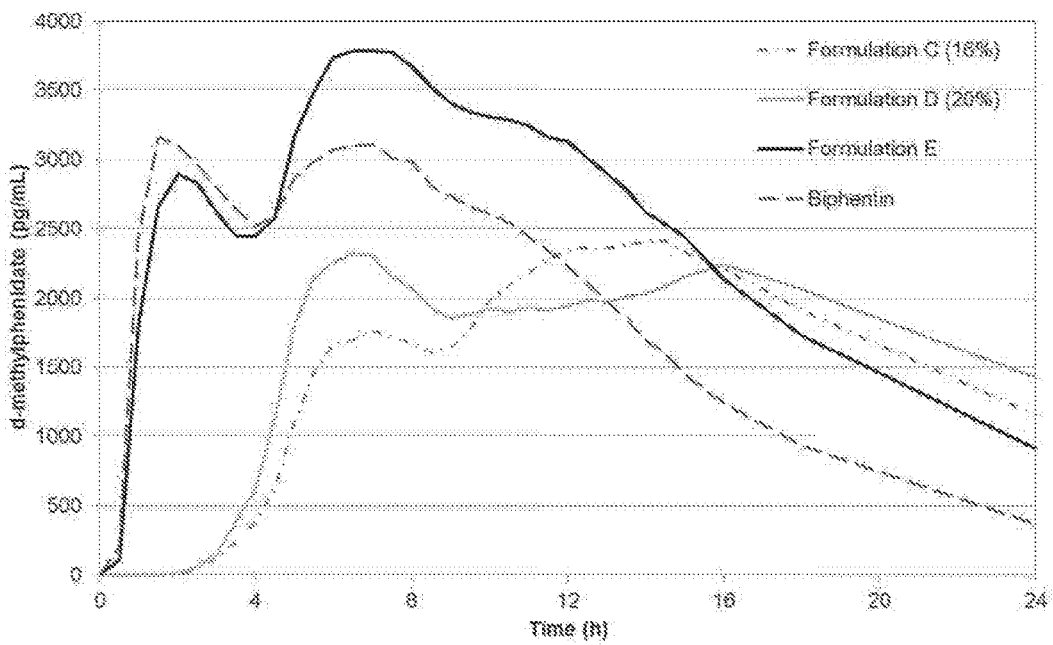

Figure 3: Results of PK Study 063-003
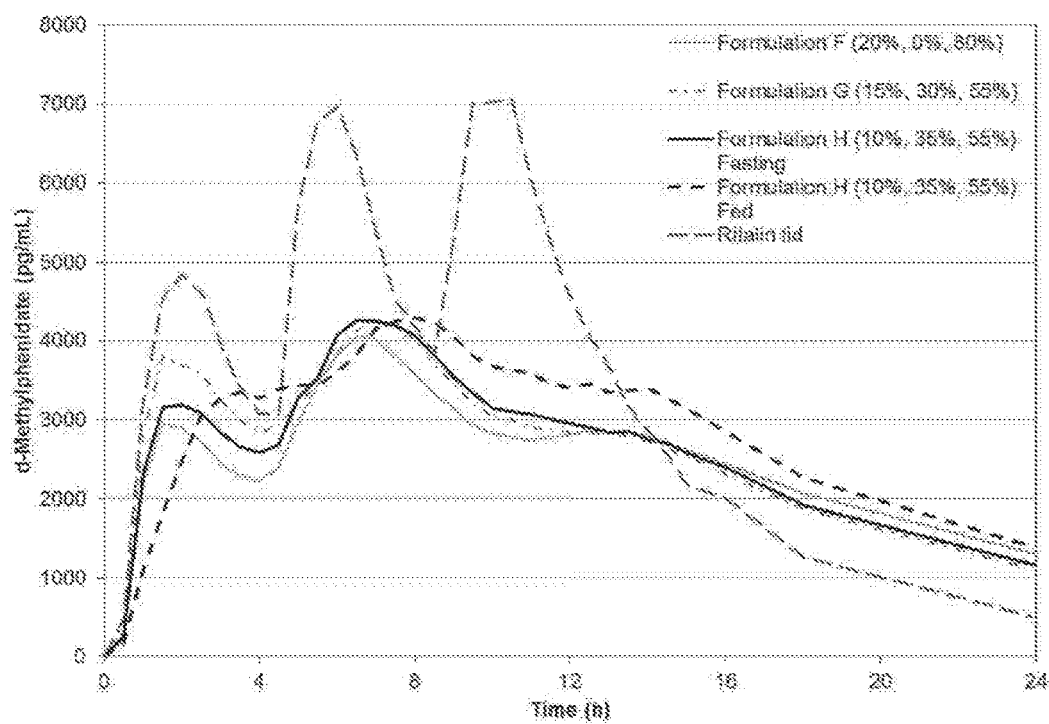
Figure 4: Results of PK Study 063-005 Formulation I (100 mg)
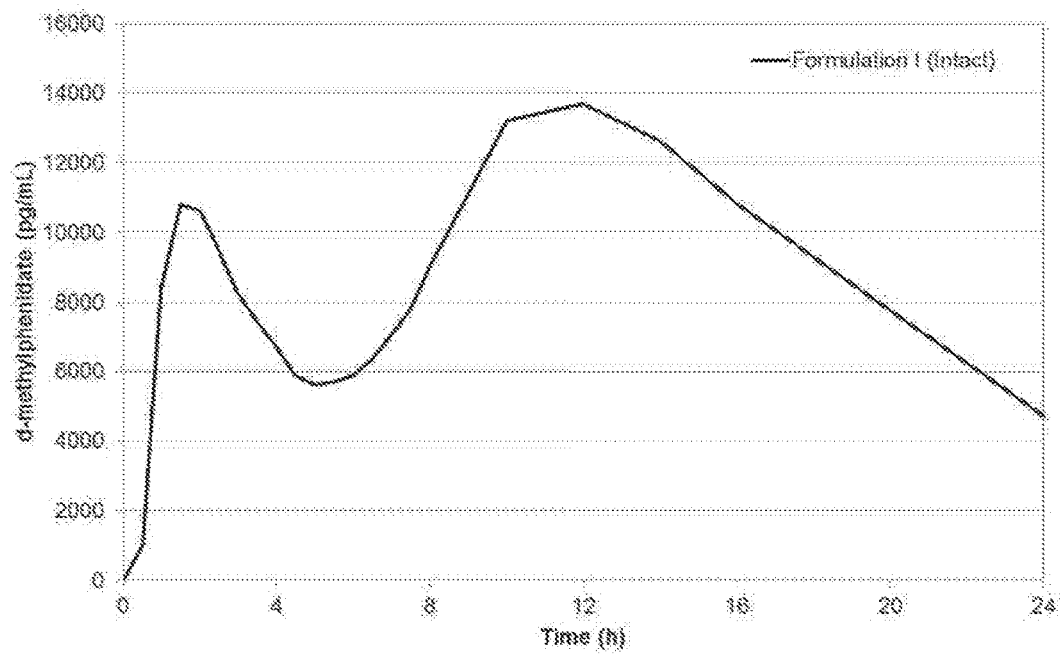

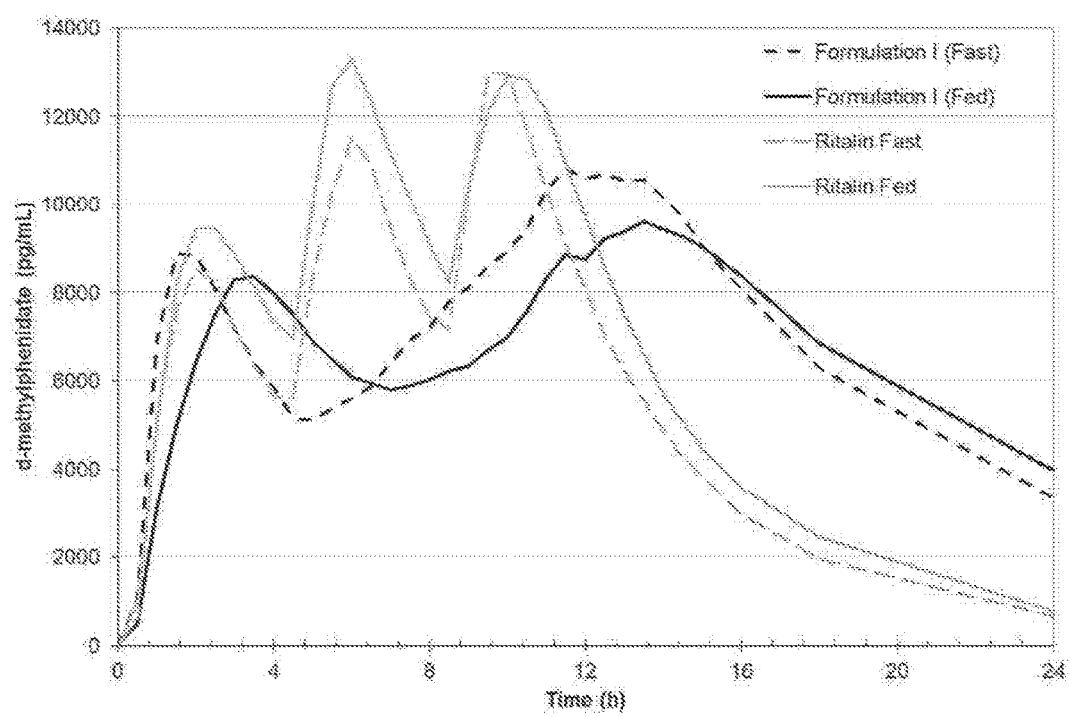

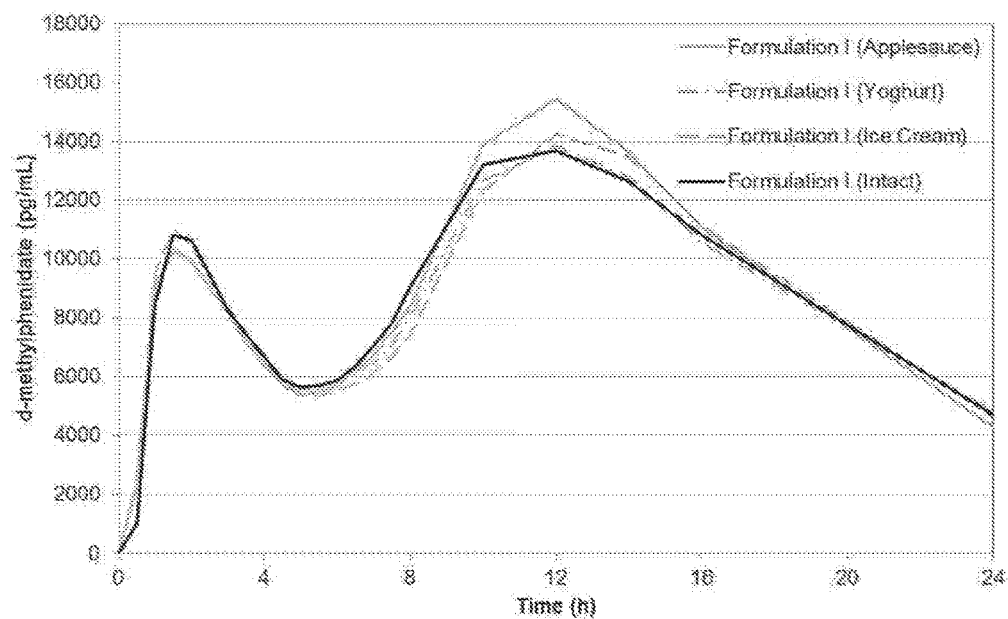
Figure 6: Results of PK Study 063-005 Sprinkle Comparison of Formulation I 100 mg

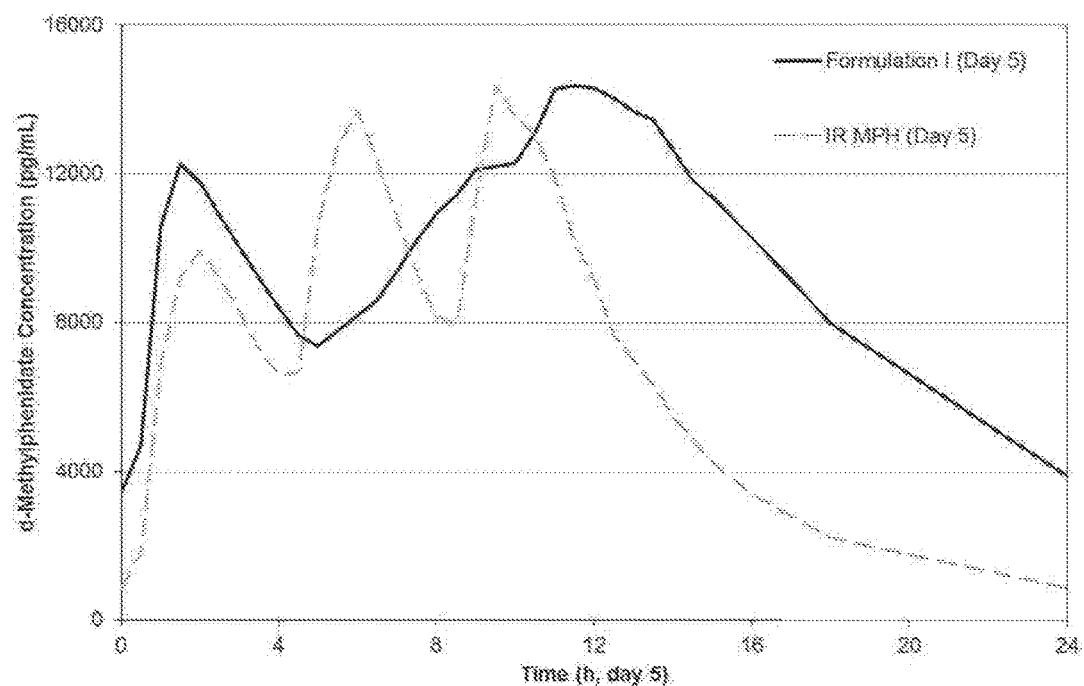
Figure 7: Results of PK Study 063-007 (Formulation I 100 mg vs Ritalin 60 mg)

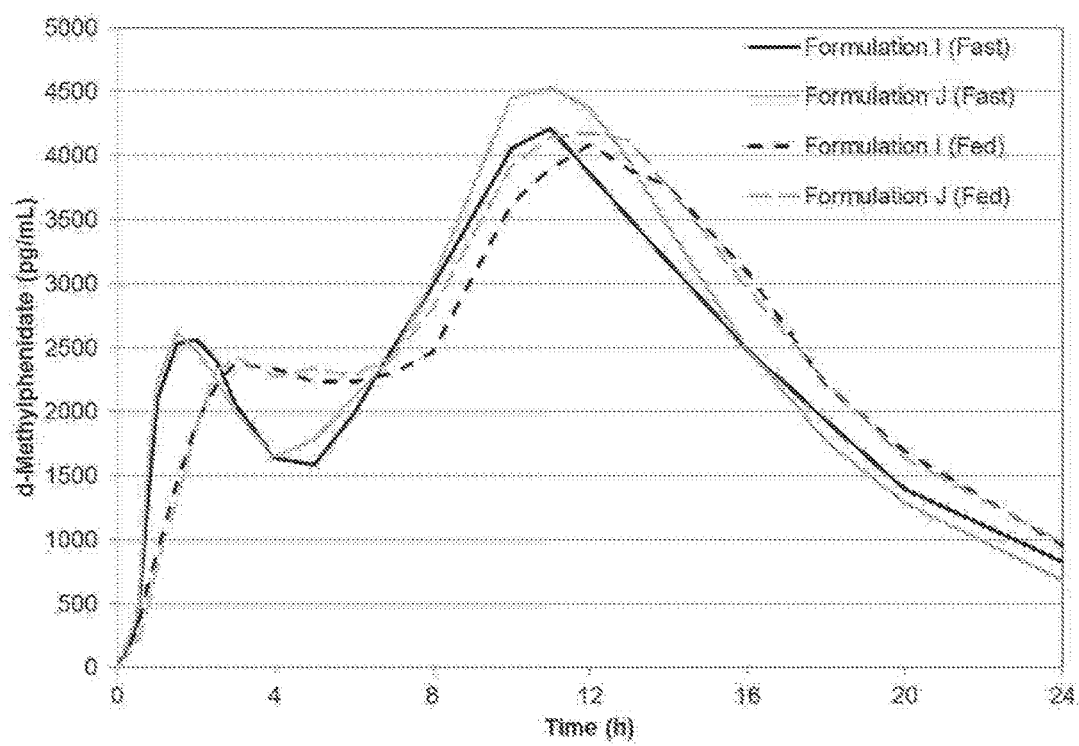
Figure 8: Results of PK Study 063-011 (Smaller Bead Formulation J)

METHODS AND COMPOSITIONS PARTICULARLY FOR TREATMENT OF ATTENTION DEFICIT DISORDER

BACKGROUND OF THE INVENTION

Field of the Invention

The present invention relates to methods and compositions, particularly for treatment of attention deficit disorder.

Description of the Prior Art

Sustained release dosage forms are important in the search for improved therapy, both through improved patient compliance and decreased incidences of adverse drug reactions.

It is the intent of sustained release formulations to provide a longer period of pharmacologic action after administration than is ordinarily obtained after administration of immediate release dosage forms. Sustained release compositions may be used to delay absorption of a medicament until it has reached certain portions of the alimentary tract, and maintain a desired concentration of the medicament in the blood stream for a longer duration than would occur if conventional rapid release dosage forms are administered. Such longer periods of response provide for many therapeutic benefits that are not achieved with corresponding short acting, immediate release preparations. Thus, therapy may be continued without interrupting the sleep of the patient, which is of special importance, for example, when treating a patient for moderate to severe pain (e.g., a post-surgery patient, a cancer patient, etc.), or for those patients who experience migraine headaches on awakening, as well as for the debilitated patient for whom sleep is essential. A further general advantage of longer acting drug preparations is improved patient compliance resulting from the avoidance of missed doses through patient forgetfulness.

Unless conventional rapid acting drug therapy is carefully administered at frequent intervals to maintain effective steady state blood levels of the drug, peaks and valleys in the blood level of the active drug occur due to rapid absorption, systemic excretion of the compound and through metabolic inactivation, thereby producing special problems in maintenance therapy of the patient.

In view of this, it is considered a goal of many skilled in the art that a controlled release dosage form will ideally provide therapeutic concentration of the drug in blood that is maintained throughout the dosing interval with a reduction in the peak/trough concentration ratio. Central to the development process are the many variables that influence the in vivo release and subsequent absorption of the active ingredients from the gastrointestinal tract.

It is known in the pharmaceutical art to prepare compositions which provide for sustained release of pharmacologically active substances contained in the compositions after oral administration to humans and animals. Sustained release formulations known in the art include specially coated pellets, coated tablets and capsules, and ion exchange resins, wherein the slow release of the active medicament is brought about through selective breakdown of the coating of the preparation or through compounding with a special matrix to affect the release of a drug. Some sustained release formulations provide for related sequential release of a single dose of an active compound at predetermined periods after administration.

Thus, sustained release dosage forms are important in the search for improved therapy, both through improved patient compliance and decreased incidences of adverse drug reactions.

While controlled and/or sustained release compositions have constituted a definite advance in the art, improvements in these compositions have been sought, particularly for preparations available for conditions such as Attention Deficit Hyperactivity Disorder (ADHD), diabetes etc.

Attention Deficit Disorders are the most common psychiatric disorders in children (Campbell et al. 1992) with reported rates ranging from 4% to 9% (Aman et al. 1983).

Attention Deficit Disorder (ADD) is characterized by inattention and impulsivity and may be present with hyperactivity (ADHD) (Shaywitz et al. 1984). Other characteristics may include aggressiveness, stealing, lying, truancy, setting fires, running away, explosiveness, cognitive and learning problems as well as poor social skills (Campbell et al. 1992). It is four to five times more frequent in boys than girls (Campbell et al. 1992).

Stimulant medication, such as amphetamines, have been shown to be the most effective agents in the treatment of children with disorders of activity modulation and attention regulation and result in significant improvement in 70 to 80 percent of affected children (Shaywitz et al. 1984). Positive effects of stimulants have been documented in a variety of areas including behavioral, social, perceptual performance, motor activity, impulse control, attention regulation and cognitive performance (Barkley 1977, Kavale 1983, Offenbacher et al. 1983, Rosenthal et al 1978).

Long thought of as a childhood disorder, ADHD is now known to persist into adolescence and adulthood (Practice Parameter for the Use of Stimulant Medications in the treatment of Children, Adolescents, and Adults. J. AM. ACAD. CHILD ADOLESC. PSYCHIATRY, 41:2 SUPPLEMENT, FEBRUARY 2002)

Methylphenidate [dl-threo-methyl-2-phenyl-2-(2-piperidyl)acetate] is the psycho-stimulant used most frequently in the treatment of hyperactivity and attention deficit disorder. It appears to have a higher incidence of positive effects and a lower incidence of adverse effects than other psychostimulants. The efficacy of methylphenidate ("MPH") in improving attention and behavioral symptoms has been supported by many studies.

Immediate release methylphenidate preparations, because of their short half-life, require frequent administration at short intervals to ensure adequate treatment throughout a child's school day, adolescence's school day (high school, college, university) and adult working day. The rapid onset and offset of immediate release methylphenidate preparations means that a medicated person with attention deficit disorder will be maximally affected only for relatively brief periods during the day. Due to its short half-life, it has been known to administer MPH given twice per day, usually once after breakfast and once during the day, an event that some children and some school personnel apparently avoid, resulting in poor compliance with prescribed regimens (Brown et al., 1985; Firestone 1982).

Compliance is a major problem for children, adolescences and adults. Poor compliance in taking medication may explain, in part, the variable and conflicting results reported in many studies of the effect of medication on improving the behavior of hyperactive children, adolescents and adults. These limitations of immediate release methylphenidate led to interest in products with longer effective periods of action.

Thus, much of the prior art has focussed on development of formulations for treatment of ADHD with a focus on administration to children and improving patient compliance in the patient population. This has led to commercialization of a number of sustained release formulations of methylphenidate—e.g., Ritalin SR™, Concerta™ and Biphentin™.

Duration of efficacy with long-acting methylphenidate formulations was maintained from one hour to 12 hours post-dosing for osmotically controlled-release oral delivery systems (four trials), 1.5 hours to 7.5 hours for methylphenidate extended release in one trial, one hour to 12 hours post-dosing for methylphenidate spheroidal oral drug absorption systems (two trials) and 30 minutes to 12 hours post-dosing for dexmethylphenidate extended release (five trials). Most long-acting stimulants conferred benefits on ADHD symptoms in patients across the age spectrum for up to 12 hours after a single morning dose as measured by the permanent product measure of performance mathematics test (PERMP). Formulations may differ in time to peak effect and maintenance of effect as well as magnitude of effect at different time points during the day (Brams M, Moon E, Pucci M, Lopez F A. Duration of effect of oral long-acting stimulant medications for ADHD throughout the day. *Curr Med Res Opin.* 2010 Aug; 26(8):1809-25. doi: 10.1185/03007995.2010.488553).

Despite the advances in the art, there is still room for improvement.

First, some or all of the commercially available sustained release formulations of methylphenidate do not have, in combination, a rapid onset of action and a duration of action that exceeds 12 hours. The provision of a sustained release formulation having this combination of features would be highly desirable for adolescents or adults whose daily activities require them to have a rapid onset of therapeutic effect and duration of action that lasts at least 14 hours to get them through the day and will into the evening without the need of another dose of the medication.

Second, some or all of the commercially available sustained release formulations of methylphenidate are susceptible to premature release of the active ingredient in a gastric environment that contains alcohol (e.g., ethanol). This can be a significant problem if the subject taking the formulation is an alcohol abuser.

This, it would be highly desirable to have a pharmaceutical composition that obviates or mitigates one or both of these problems in the prior art.

SUMMARY OF THE INVENTION

It is an object of the present invention to obviate or mitigate at least one of the above-mentioned disadvantages of the prior art.

It is another object of the present invention to provide a novel coated bead.

It is another object of the present invention to provide a novel solid oral pharmaceutical composition.

Accordingly, in one of its aspects, the present invention provides a coated bead comprising:

(a) a granule;

(b) a first layer coated over the granule, the first layer comprising a first amount of an active pharmaceutical ingredient comprising a central nervous system stimulant;

(c) a second layer coated over the first layer, the second layer being present in an amount sufficient to substantially delay release of the active pharmaceutical ingredient in the first layer until after the coated bead reaches a distal intestine portion of a subject to whom the coated bead is administered; and (d) a third layer coated over the second layer, the third layer comprising a second amount of the active pharmaceutical ingredient, the third layer being configured to permit substantially immediate release of the active pharmaceutical ingredient comprised therein.

In another of its aspects, the present invention provides a an oral solid pharmaceutical composition comprising a first plurality of coated beads and a second plurality of coated beads, wherein:

each coated bead in the first plurality of coated beads comprising: a first granule and a first layer coated over the first granule, the first layer comprising an active pharmaceutical ingredient comprising a central nervous system stimulant, the first plurality of coated beads being configured to provide substantially immediate release of the active pharmaceutical ingredient; and each coated bead in the second plurality of coated beads comprising: a second granule; a first layer coated over the granule, the first layer comprising an active pharmaceutical ingredient comprising a central nervous system stimulant; and a second layer coated over the first layer, the second layer being present in an amount sufficient to substantially delay release of the active pharmaceutical ingredient in the first layer until after the coated bead reaches a distal intestine portion of a subject to whom the coated bead is administered, the coated bead being substantially free of an outer layer configured to provide substantially immediate release of the active pharmaceutical ingredient.

In yet another of its aspects, the present invention provides an oral solid pharmaceutical composition comprising a first plurality of coated beads, a second plurality of coated beads and a third plurality of coated bead, wherein:

each coated bead in the first plurality of coated beads comprising: a first granule and a first layer coated over the first granule, the first layer comprising an active pharmaceutical ingredient comprising a central nervous system stimulant, the first plurality of coated beads being configured to provide substantially immediate release of the active pharmaceutical ingredient;

each coated bead in the second plurality of coated beads comprising: a second granule; a first layer coated over the granule, the first layer comprising an active pharmaceutical ingredient comprising a central nervous system stimulant; and a second layer coated over the first layer, the second layer being present in an amount sufficient to substantially delay release of the active pharmaceutical ingredient in the first layer; and each coated bead in the third plurality of coated beads comprising: a third granule; a first layer coated over the granule, the first layer comprising an active pharmaceutical ingredient comprising a central nervous system stimulant, a second layer coated over the first layer, the second layer being present in an amount sufficient to substantially delay release of the active pharmaceutical ingredient in the first layer until after the coated bead reaches a distal intestine portion of a subject to whom the coated bead is administered.

In yet another of its aspects, the present invention provides a coated bead comprising:

(a) a granule;

(b) an inner layer coated over the granule, the inner layer comprising an active pharmaceutical ingredient comprising a central nervous system stimulant; and (c) an outer delayed release layer coated over inner layer which is substantially free of a salt of alginic acid;

wherein release of the active pharmaceutical ingredient is not more than 20% when measured under in vitro conditions with stirring at 100 rpm at pH 1.2 for 2 hours in 900 mL of a medium comprising up to about 35% v/v ethanol In yet another of its aspects, the present invention provides a coated bead comprising:

(a) a granule;

(b) an inner layer coated over the granule, the inner layer comprising an active pharmaceutical ingredient comprising a central nervous system stimulant; and (c) an outer delayed release layer coated over inner layer, the outer delayed release coating comprises an anionic copolymer based on methyl acrylate, methyl methacrylate and methacrylic acid with the proviso that the outer delayed release layer is substantially free of a salt of alginic acid, the outer delayed release layer being present at an average thickness in the range of of from about 5 µm to about 50 µm.

In yet another of its aspects, the present invention provides a coated bead comprising:

(a) a granule comprising a first amount of an active pharmaceutical ingredient comprising a central nervous system stimulant (e.g., the granule can comprise a granule substrate in admixture with the active pharmaceutical ingredient or the active pharmaceutical ingredient could be coated over the granule substrate); and (b) a first layer coated over the granule, the first layer being present in an amount sufficient to substantially delay release of the active pharmaceutical ingredient in the first layer until after the coated bead reaches a distal intestine portion of a subject to whom the coated bead is administered; and (c) a second layer coated over the first layer, the second layer comprising a second amount of the active pharmaceutical ingredient, the second layer being configured to permit substantially immediate release of the active pharmaceutical ingredient comprised therein.

Throughout this specification, the term "coated over" (or the functional equivalent thereof) is used to describe a first layer of material disposed exteriorly with respect to a second layer of material. It should be clearly understood that, in such a case, the first layer layer of material may be directly coated over (i.e., in contacting relation with) the second layer of material or indirectly coated over (i.e., in non-contacting relation with) the second layer of material. An example of the "indirectly coated over" would be when the first layer of material and the second layer of material has disposed between them one or more intermediate layers of material. The point is the term "coated over" (or the functional equivalent thereof), when used on its own encompasses both "directly coated over" and "indirectly coated over" described above.

The present inventors have developed a novel coated bead and a novel pharmaceutical composition which are believed to obviate or mitigate one or both of the above-mentioned disadvantages described above with reference to some or all of the commercially available sustained release formulations of methylphenidate. The present coated bead and pharmaceutical composition are believed to be highly advantageous in that they have a rapid on set of action (e.g., approximately 1 hour after administration) and a long duration of action (e.g., approximately 16 hours or more) after reaching steady state in the subject. While not wishing to be bound by any particular theory or mode of action, it is believed that the long duration of action results in a blood plasma concentration of the active ingredient at 24 hours after administration which allows for a rapid onset of action when another dose of the active ingredient is taken—i.e., there appears to be a baseline blood plasma concentration of the active ingredient when it is time to take a subsequent dose to allow for a rapid onset of action of that subsequent dose.

The present coated bead and pharmaceutical composition are believed to address a limitation of some or all current commercially available long-acting methylphenidate formulations which are not reported to provide and maintain duration of action beyond 12 hours. The present coated bead and pharmaceutical composition are also believed to address the limitation with long-acting lisdexamfetamine dimesylate that is reported to last up to 14 hours but do not have a rapid onset of action. These two characteristics (rapid onset of action and long duration of action) of the present coated bead and pharmaceutical composition are believed to address a significant limitation for adolescences or adults whose daily activities require them to have a rapid onset of therapeutic effect and duration of action that lasts at least 14 hours to get them through the day and will into the evening without the need of another dose of the medication.

In one preferred embodiment, the present coated bead and pharmaceutical composition are characterized by having a resistance release of the active ingredient in an aqueous composition comprising up to about 35% by volume of an alcohol (e.g., ethanol)—i.e., release of the active pharmaceutical ingredient is not more than 20% when measured under in vitro conditions with stirring at 100 rpm at pH 1.2 for 2 hours in 900 mL of a medium comprising up to about 35% v/v ethanol. This resistance to alcohol-related release of the active pharmaceutical ingredient can be achieved without the need to use coating layer comprising one or more salts of aglinic acid thereby simplifying manufacturing costs and the like.

BRIEF DESCRIPTION OF THE DRAWINGS

Embodiments of the present invention will be described with reference to the accompanying drawings, wherein like reference numerals denote like parts, and in which:

FIGS. 1-10 illustrate results on testing done on formulations produced in the examples described below.

DETAILED DESCRIPTION OF THE PREFERRED EMBODIMENTS

Figure 9:
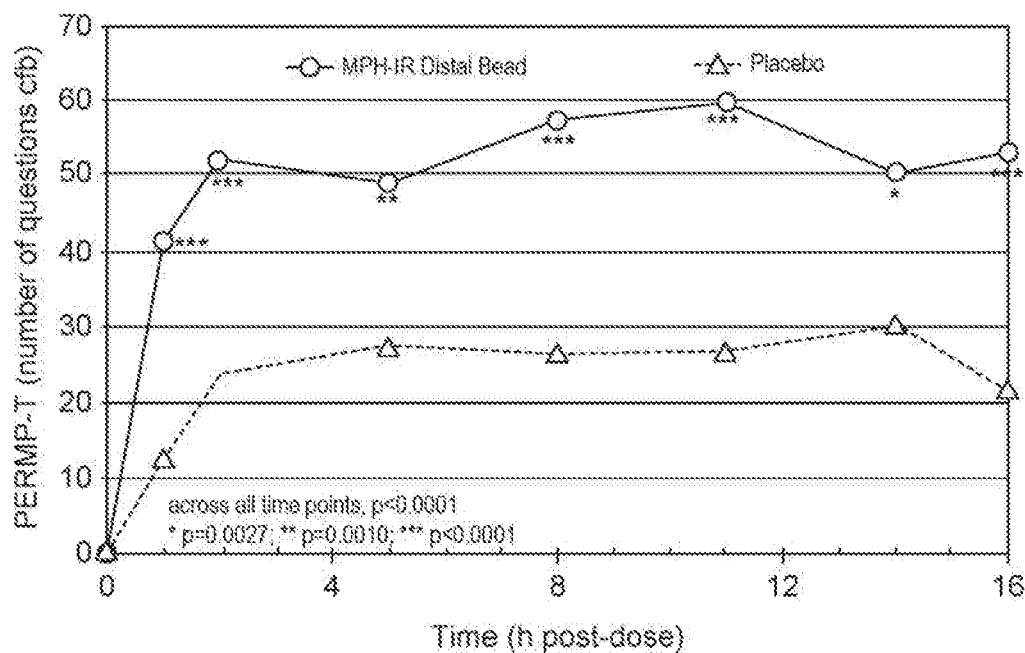

The coated bead and solid oral pharmaceutical compositions of the present invention include a central nervous system stimulant which can be generally defined as a chemical entity that affects the dopamine or norepinephrine neural pathways. Preferred pharmaceutically active ingredients include, but are not limited to amphetamine, dextroamphetamine, the active isomers of amphetamines and amphetamine salts including salts of dextroamphetamine, methylphenidate and its active salts, or combinations thereof, all of which can be used as racemic mixtures or pure isomers such as d-threo methylphenidate, or a prodrug or pharmaceutical salt, or mixed pharmaceutical salts of any thereof alone or in combination. The disclosed coated bead and solid oral pharmaceutical compositions can also include a prodrug, including but not limited to amino acid conjugated active ingredients such as 1-lysine-d-amphetamine.

Conditions or disorders that can be treated using the present coated bead or solid oral pharmaceutical compositions include, but are not limited to attention deficit disorder (ADD), attention deficit hyperactivity disorder (ADHD), excessive daytime sleepiness, major depressive disorder, bipolar depression, negative symptoms in schizophrenia, chronic fatigue, fatigue associated with chemotherapy or binge eating disorder. Attention deficit disorders are characterized by hyperactive, impulsive or inattentive symptoms that cause impairment in social, academic, or occupational functioning, and are often present in two or more settings, school (or work) and at home, for example. For the Inattentive Type, at least 6 (5 for adults >18 years of age) of the following symptoms have persisted for at least 6 months: lack of attention to details/careless mistakes; lack of sustained attention; poor listener; failure to follow through on tasks; poor organization; avoids tasks requiring sustained mental effort; loses things; easily distracted; and forgetful. For the Hyperactive-Impulsive Type, at least 6 (5 for adults >18 years of age) of the following symptoms have persisted for at least 6 months: fidgeting/squirming; leaving seat; inappropriate running/climbing; difficulty with quiet activities; "on the go;" excessive talking; blurting answers; can't wait turn, and intrusive. The combined type includes both inattentive and hyperactive-impulsive behaviors.

It is understood that the term treatment as used herein is not limited to the cure or elimination of any condition or disorder nor is that term limited to the achievement of certain milestones or improvement criteria in a particular subject, but includes the administration of an agent for the purpose of achieving positive effects in terms of cognitive or behavioral function, reduction of symptoms or side effects. All such activities are considered to be treatment whether or not any improvement is immediately observable or measureable.

In a highly preferred embodiment, the present invention relates to a controlled release oral formulation of methylphenidate (or a pharmaceutically acceptable salt thereof) that provides a rapid onset of therapeutic effect and a gradual drop in plasma concentration after a prolonged period of therapeutic effect (e.g., 16 hours). This oral formulation comprises a plurality of substrates, preferably in the form of coated beads. Preferably, the coated bead comprises: (i) an initial portion of an effective dose of methylphenidate (or a pharmaceutically acceptable salt thereof) in immediate release form coated over granule; (ii) a controlled release (e.g., hydrophobic) material, preferably in the form of an acrylic polymer, coated over (i); (iii) a delayed (or distal) release (e.g., colonic delivery) coating over (ii) in an amount sufficient to substantially delay the release of the drug from the substrate until after coated bead passes through the stomach and the distal part of the gastrointestinal tract; and, optionally, (iv) a remaining portion of the effective dose of methylphenidate (or a pharmaceutically acceptable salt thereof) in immediate release form coated over (iii).

Preferably, the colonic delivery coating is derived from an aqueous dispersion of an anionic copolymer based on methyl acrylate, methyl methacrylate and methacrylic acid, a plasticizer and a glidant. The contents of the encapsulated product may be sprinkled on soft foods before administration.

The substrate (e.g., granules) can be chosen from spheres, also referred as pellets, also referred as beads, made of microcrystalline cellulose, mannitol-PVP, silica, starch, lactose, calcium carbonate or combination thereof. The preferred substrate to be used is sugar spheres 14/18 mesh to 18/20 mesh.

It can be preferred to use sugar spheres 14/18 mesh to 18/20 mesh amount of about 20% to about 70% by weight, of about 25% to about 65% by weight, of about 40% to about 64% by weight, of about 41% to about 63% by weight, of about 42% to about 62% by weight, of about 43% to about 61% by weight, based on the weight of the pharmaceutical composition. An amount of about 44.0% to about 53.5% by weight based on the weight of the pharmaceutical composition can be preferred of the nonpareil substrate, particularly of sugar spheres 14/18 mesh to 18/20 mesh.

The controlled release polymer can include ethylcellulose polymers, cellulose ethers (e.g., hydroxypropyl methylcellulose, hydroxypropylcellulose, methylcellulose, hydroxyethylcellulose, etc.), polyethylene oxide, polyvinyl alcohol derivates, methacrylic acid copolymers (e.g., poly(ethylene glycol) diacrylate, poly(ethylene glycol) triacrylate, poly(ethylene glycol) dimethacrylate, poly(ethylene glycol) trimethacrylate, polymulti (meth)acrylates], polyethylene glycol, polyglycolic acid, polylactic acid, poly caprolactone, poly(n-hydroxybutyrate), polyamino acids, poly(amide-enamines), poly(esters)[1], ethylene-vinyl acetate (EVA), polyvinyl pyrrolidone (PVP), poly acrylic acid (PAA), poly methacrylic acid (PMAA) or combinations thereof in amounts that would deliver the active pharmaceutical ingredient at the desired release rate. Preferably, the controlled release polymer is derived from a mixture copolymer of ethyl acrylate, methyl methacrylate and methacrylic acid ester with quaternary ammonium groups (Ammonio Methacrylate Copolymer, Type B USP/NF).

[1] *Chem. Rev.* 1999, 99, 3181-3198. Polymeric Systems for Controlled Drug Release (Uhrich et al.)

It can be preferred to use ammonio methacrylate copolymer, Type B USP/NF as a controlled release material. Such a material is commercially available from Evonik under the tradement name Eudragit® RS30D.

It thus can be preferred to use a controlled release polymer amount of about 3% to about 16% by weight, of about 4% to about 15% by weight, of about 5% to about 14% by weight, of about 5.1% to about 13.5% by weight, such as of about 8.0% by weight, of about 8.1% by weight, of about 8.2% by weight, of about 8.3% by weight, of about 8.4% by weight, of about 8.5% by weight, of about 8.6% by weight, of about 8.7% by weight, of about 8.8% by weight, of about 8.9% by weight or about 9.0% by weight, of about 9.1% by weight, of about 9.2% by weight, of about 9.3% by weight, of about 9.4% by weight, of about 9.5% by weight, of about 9.6% by weight, of about 9.7% by weight, of about 9.8% by weight, of about 9.9% by weight Chem. Rev. 1999, 99, 3181-3198. Polymeric Systems for Controlled Drug Release (Uhrich et al.) of about 10.0%, of about 10.1% by weight, of about 10.2% by weight, of about 10.3% by weight, of about 10.4% by weight, of about 10.5% by weight, of about 10.6% by weight or of about 10.7% by weight, based on the weight of the pharmaceutical composition and the coated bead.

An amount of about 10.0% to about 10.7% by weight based on the weight of the pharmaceutical composition can be preferred, particularly of ammonio methacrylate copolymer, Type B USP/NF is used as controlled release modifier. The aforementioned amounts refer to the amount of all controlled release (e.g., hydrophobic) materials in the pharmaceutical composition or coated bead.

The delayed (or distal) release (e.g., colonic delivery) coating material can include guar gum, pectin, hydroxypropyl methylcellulose phthalate, cellulose acetate phthalate, cellulose acetate trimelliate, biodegradable polysaccharides (amylose, arabinogalactan, chitosan, chondroitin sulfate, cyclodextrine, dextran, guar gum, pectin, xanthan gum, xylan), poly(methacylic acid-co-methyl methacrylate) 1:2, poly(methacylic acid-co-methyl methacrylate) 1:1, polyvinyl acetate phthalate, covalent linkage of the drug with carrier (azo conjugates, cyclodextrine conjugates, glycoside conjugates, glucuronate conjugates, dextran conjugates, polypeptide conjugates, polymeric drugs), acidic comonomers, methacryloyloxy azobenzene and 2-hydroxyethyl methacrylate (HEMA), dextran hydrogels, and combinations thereof in amounts that would control the delivery of the product to the distal part of the GI tract. The preferred system to be used is the anionic copolymer based on methyl acrylate, methyl methacrylate and methacrylic acid (IUPAC name: Poly(methyl acrylate-co-methyl methacrylate-co-methacrylic acid) 7:3:1).

It can be preferred to use poly(methyl acrylate-co-methyl methacrylate-co-methacrylic acid) 7:3:1 as the delayed (or distal) release (e.g., colonic delivery) material. Such a material is commercially available from Evonik under the tradement name Eudragit® FS30D.

It thus can be preferred to use a distal release modifier amount of about 3% to about 20% by weight, of about 8% to about 18% by weight, of about 10% to about 17% by weight, of about 10.1% to about 16.5 by weight, such as of about 15.0% by weight, of about 15.1% by weight, of about 15.2% by weight, of about 15.3% by weight, of about 15.4% by weight, of about 15.5% by weight, of about 15.6% by weight, of about 15.7% by weight, of about 15.8% by weight, of about 15.9% by weight or about 16.0% by weight, of about 16.1% by weight, of about 16.2% by weight, of about 16.3% by weight, of about 16.4% by weight based on the weight of the pharmaceutical composition.

An amount of about 15.0% to about 16.0% by weight based on the weight of the pharmaceutical composition can be preferred, particularly of poly(methyl acrylate-co-methyl methacrylate-co-methacrylic acid) 7:3:1 is used as distal release modifier. The aforementioned amounts refer to the amount of all delayed (or distal) release (e.g., colonic delivery) materials (i.e., including mixtures) in the pharmaceutical composition and the coated bead.

Plasticizers can may optionally be used. Examples of useful plasticizers include citrates (triethyl citrate, acetyl Triethyl citrate, tributyl citrate and acetyl tributyl citrate, acetyl tributyl citrate), triacetin, dibutyl sebacate, sebacate and azelate esters (di-2-ethylhexyl sebacate, di-2-ethylhexyl azelate, diisodecyl sebacate), ester of glycol and polyhydric alcohol [propylene glycol, glycerol (glycerin), polyethylene glycol, glyceryl triacetate], glyceryl monostearate (GMS), polysorbate 80, phthalates (di-octyl phthalate, diisodecyl phthalate, diisononyl phthalate), dibutyl phthalate, diethyl phthalate, adipates, phosphate esters, Polymerics, trimellitates (tris-2-ethylhexyltrimelliate), glutarates, castor oil, acetylated monoglycerides, fractionated coconut oil and mixtures of any two or more thereof. The preferred plasticizers to be used are triethyl citrate, glyceryl monostearate in combination with polyoxyethylene (20) sorbitan monooleate (Polysorbate 80™).

It can be preferred to use triethyl citrate and glyceryl monostearate emulsion as plasticizer system.

It thus can be preferred to use a plasticizer system amount of about 0.1% to about 10% by weight, of about 0.5% to about 9% by weight, of about 1% to about 7% by weight, of about 2% to about 6% by weight, of about 2.5% to about 5.5% by weight, of about 3.5% to about 4.5% by weight such as of about 3.6% by weight, of about 3.7% by weight, of about 3.8% by weight, of about 3.9% by weight, of about 4.0% by weight, of about 4.1% by weight, of about 4.2% by weight, of about 4.3% by weight, of about 4.4% by weight, of about 4.5% by weight based on the weight of the pharmaceutical composition.

An amount of about 4.0% to about 4.5% by weight based on the weight of the pharmaceutical composition can be preferred, particularly of triethyl citrate and glyceryl monostearate emulsion is used as plasticizer system. The aforementioned amounts refer to the amount of all plasticizers (i.e., including mixtures) in the composition.

Glidants can include talc, fumed silica, lecithin. The preferred glidants to be used are talc and fumed silica.

Binders can include hydroxypropyl cellulose (HPMC), hydroxypropyl cellulose (HPC), polyvinyl pyrollidone, carbopol, and combinations thereof. It can be preferred to use HMPC as a binder.

It thus can be preferred to use a binder amount of about 1% to about 10% by weight, of about 2% to about 9% by weight, of about 3% to about 7% by weight, of about 3% to about 6% by weight, such as of about 3.0% by weight, of about 3.1% by weight, of about 3.2% by weight, of about 3.3% by weight, of about 3.4% by weight, of about 3.5% by weight, of about 3.6% by weight, of about 3.7% by weight, of about 3.8% by weight, of about 3.9% by weight, of about 4.0% by weight, of about 4.1% by weight, of about 4.2% by weight, of about 4.3% by weight, of about 4.4% by weight, of about 4.5% by weight, of about 4.6% by weight, of about 4.7% by weight, of about 4.8% by weight, of about 4.9% by weight or of about 5.0% by weight, of about 5.1% by weight, of about 5.2% by weight, of about 5.3% by weight, of about 5.4% by weight, of about 5.5% by weight, of about 5.6% by weight, of about 5.7% by weight, of about 5.8% by weight, of about 5.9% by weight or of about 6.0% by weight, based on the weight of the pharmaceutical composition.

An amount of about 3.8% to about 6.0% by weight based on the weight of the pharmaceutical composition can be preferred, particularly of HPMC is used as binder. The aforementioned amounts refer to the amount of all binders (i.e., including mixtures) in the composition.

It is preferred to use an outer layer of immediate release methylphenidate HCl amount of about 1% to about 30% by weight, of about 5% to about 28% by weight, of about 15% to about 27% by weight, of about 18% to about 25% by weight, such as of about 19.0% to about 25.0% by weight, of about 19.1% by weight, of about 19.2% by weight, of about 19.3% by weight, of about 19.4% by weight, of about 19.5% by weight, of about 19.6% by weight, of about 19.7% by weight, of about 19.8% by weight, of about 19.9% by weight, of about 20.0% by weight, of about 20.1% by weight, of about 20.2% by weight, of about 20.3% by weight, of about 20.4% by weight, of about 20.5% by weight, of about 20.6% by weight, of about 20.7% by weight, of about 20.8% by weight, of about 20.9% by weight or of about 21.0% by weight, of about 21.1% by weight, of about 21.2% by weight, of about 21.3% by weight, of about 21.4% by weight, of about 21.5% by weight, of about 21.6% by weight, of about 21.7% by weight, of about 21.8% by weight, of about 21.9% by weight or of about 22.0% by weight, based on the weight of the pharmaceutical composition. An amount of about 18.0% to about 22.0% by weight based on the weight of the pharmaceutical composition can be preferred. The aforementioned amounts refer to the amount of methylphenidate hydrochloride or its respective amount of the base or any of its salts in the outer immediate release layer composition.

It is also preferred to use an inner core layer of immediate release methylphenidate HCl amount of about 1% to about 99% by weight, of about 5% to about 95% by weight, of about 60 to about 90% by weight, of about 70% to about 85% by weight, such as of about 73.0% to about 83.0% by weight, of about 79.0% by weight, of about 79.1% by weight, of about 79.2% by weight, of about 79.3% by weight, of about 79.4% by weight, of about 79.5% by weight, of about 79.6% by weight, of about 79.7% by weight, of about 79.8% by weight, of about 79.9% by weight, of about 80.0% by weight, of about 80.1% by weight, of about 80.2% by weight, of about 80.3% by weight, of about 80.4% by weight, of about 80.5% by weight, of about 80.6% by weight, of about 80.7% by weight, of about 80.8% by weight, of about 80.9% by weight or of about 81.0% by weight, of about 81.1% by weight, of about 81.2% by weight, of about 81.3% by weight, of about 81.4% by weight, of about 81.5% by weight, of about 81.6% by weight, of about 81.7% by weight, of about 81.8% by weight, of about 81.9% by weight or of about 82.0% by weight, based on the weight of the pharmaceutical composition. An amount of about 78.0% to about 82.0% by weight based on the weight of the pharmaceutical composition can be preferred. The aforementioned amounts refer to the amount of methylphenidate hydrochloride or its respective amount of the base or any of its salts in the inner core immediate release layer composition.

As described above, several solid dose controlled-release formulations of some or all commercially available methylphenidate are commercially available in the market. However, the therapeutic effect of some or all of those formulations is not expected to last for more than 12 hours after administration.

An advantage of the highly preferred embodiment of the present invention is believed to be that the formulation that will have a therapeutic effect of at least 14 hours of duration or more. To achieve this, the delivery of methylphenidate in the distal part of the GI tract was investigated to prolong the duration of action of the drug. The present inventors are unaware of an example of actual reported example the delivery of methylphenidate in the distal part of the GI tract. Also, no relevant in vivo data was found reporting the release of methylphenidate or its pharmaceutically acceptable salts in the distal part of the GI tract.

Methylphenidate hydrochloride is freely soluble in water and methanol, soluble in alcohol, slightly soluble in chloroform and acetone; melts between 224-226° C.; and has a pKa of approximately 8.8. Methylphenidate is relatively stable in acidic solutions but it is degraded extensively in basic solutions. The degradation occurs via the hydrolysis of the methyl ester to the free acid, α-phenyl 1-2-piperidineacetic acid. Therefore, the degradation amount increases up to 100% as the pH increases to 8.9. See *Chemical Stability of Pharmaceuticals a Handbook for Pharmacists* 1986, 587-590 (Kenneth A. Connors, Gordon L. Amidon and Valentino J. Stella) and *Analytical Profiles of Drug Substances*. 1981, 473-497. Gandharva R. Padmanabhan for additional information.

As a result, it was not known whether methylphenidate could be absorbed systematically in sufficient amount to have therapeutic effect at distal locations within the GI tract where the pH is known to be above pH 6.0. Thus, the present inventors performed in vitro and in vivo studies to determine the amount released and the extent of absorption of several methylphenidate controlled release formulations. Table 1 shows some of the different formulations explored; Table 2 shows their correspondent in vitro dissolution data and FIGS. 1-4 shows their respective in vivo results.

The preferred oral dosage form of the present invention is a capsule containing multilayer release (MLR) beads which have multiple layers to achieve the desire release rate profile of methylphenidate hydrochloride. Some of those layers have immediate release and controlled release components. It is made up of a controlled release bead which is coated to delay dissolution until it has reached the distal part of the GI tract. The distal coated controlled release bead has an immediate release topcoat to provide an initial rate of absorption needed to have the desired therapeutic effect. In a highly preferred embodiment, the immediate release component represents 20% of the total dose per bead and the controlled release component represents 80% of the total dose per bead. This formulation is designed to produce rapid rise to therapeutic plasma levels after oral administration, due to the rapid dissolution and absorption of the outer immediate release layer, followed by a period of minimum absorption and then controlled release of the immediate release core, plasma levels would then gradually decrease according to the elimination kinetics of methylphenidate.

In a preferred embodiment, the pharmaceutical dosage forms comprise methylphenidate or a pharmaceutical acceptable salt or derivate thereof as the sole pharmaceutically active agent.

The pharmaceutical composition of methylphenidate HCl, Controlled Release Capsules (e.g., Formulation I and J 80:20 described below) MPH IR distal beads may comprise about 1 to 150 mg such as about 15 mg, 25 mg, 30 mg, 35 mg, 45 mg, 55 mg 70 mg, 85 mg 100 mg and 120 mg The present coated beads are preferably formulated as a single multilayer coated bead into an oral solid pharmaceutical compositions, preferably in the form of a capsule. The capsule material is preferably a hard gelatin capsule or a hard HPMC capsule. Other capsule materials may also be used and the selection thereof is within the purview of a person of ordinary skill in the art.

In other embodiments of the present invention, it may be preferred to provide an outer layer on the coated bead, wherein the outer layer comprises one or more salts of alginic acid. The salts of alginic acid may be selected from sodium alginate, potassium alginate, magnesium alginate, lithium alginate or ammonium alginate or mixtures thereof. Preferably, the salts of alginic acid may have a viscosity of 30 to 720, preferably 40 to 450, preferably 40 to 400 or preferably 50 to 300 centipoise (cp) of a 1% aqueous solution (weight/weight). The provision of such an outer layer can improve the coated bead resistance to alcohol (e.g., ethanol) in concentrations of greater than 35% (volume/volume)—e.g., 40% (volume/volume)—since such the presence of alcohol (e.g., ethanol) in the gastric fluid usually leads to an increase to the release rates in the stomach. Due to distribution effect, the effect of ingested ethanol in the intestine is not of the same importance as in the stomach. A preferred embodiment of the invention relates to the use of coating layers described above in the coated bead to confer resistance to alcohol (e.g., ethanol) in concentrations of up to about 35% (volume/volume) in the gastric fluid without the need to use a coating comprising one or more salts of alginic acid. Thus an effective protection against the influence of ethanol should prevent such an undesired increase of pharmaceutical or nutraceutical active ingredient in the stomach in the first place. Furthermore it may be desired that protection against the influence of ethanol shall at least not influence the comparably fast release rates at pH 6.8 in media without ethanol.

Embodiments of the present invention will be illustrated with references to the following examples which should not be used to limit or otherwise construe the invention.

In the examples the following abbreviations are used:

IR beads—these are beads coated with the methylphenidate hydrochloride (MPH) and having no controlled or delayed release coating;

CRIR beads—these are IR beads which have been coated with a controlled release coating;

ECCRIR—these are CRIR beads which have been coated with an enteric coating (similar to commercially available Biphentin® product);

DRIR beads—these are IR beads which have been coated with a delayed or distal release coating;

DRCRIR beads—these are CRIR beads which have been coated with a delayed (enteric coating [ECCRIR]) or distal release coating; and MPH IR distal beads—these are DRCRIR beads which have been coated with an immediate release layer of MPH.

Various of these beads were coated with sodium alginate which can confer resistance to 40% alcohol.

The general method of manufacture of Formulation I or Formulation J is described below followed by the various studies and findings.

The MPH IR distal beads were manufactured in four different stages involving separate coating process at each stage—immediate-release coating (drug layering [IR]), controlled-release coating [CR], distal release coating [DR] and top immediate release coating [CRDRIR]. All four stages are carried out in a fluid bed dryer with Wurster column. More detailed information of the process parameters used at each stage of the manufacturing process is found in Tables 9-12, respectively.

In some cases, a layer of sodium alginate-talc is also applied as a fifth stage on top of the top immediate release coating to improve dose dumping of methylphenidate HCl in hydro-ethanolic solutions compared with coated bead formulations that do not have a layer comprising one or more salts of alginic acid without affecting the immediate release performance of the top immediate release coating. More detailed information of the process parameters used at this stage of the manufacturing process is found in Table 13.

The following is a description of the manufacturing process.

EXAMPLE 1—IR Beads

The following protocol was used to produce the IR beads.

Add Opadry clear YS-1-7006 to water and mix, then add methylphenidate hydrochloride and stir until a clear solution is obtained.

Charge fluid bed dryer (FBD) equipped with Wurster column with sugar spheres 14-18 or 18-20 mesh.

Coat the beads at an inlet temperature of 65°±10° C. and product temperature of 37.5°±3.5° C. by spraying the solution of methylphenidate hydrochloride.

After completion of the spraying process, allow the beads to dry at 41°±4° C. for approximately 3 minutes.

Cool the beads to 30°±1° C. product temperature and weigh.

EXAMPLE 2—CRIR Beads

The following protocol was used to produce the methylphenidate CR beads.

Prepare a coating dispersion by mixing Plasacryl T20, filtered (250 micrometer screen) Eudragit RS 30 D and Triethyl Citrate in a container for at least 60 minutes.

Charge fluid bed dryer (FBD) equipped with Wurster column with IR beads.

Coat the IR beads at product temperature of 25°±5° C. by spraying the coating dispersion.

After completion of the coating dispersion, spray rinse water at a product temperature of 25°±5° C.

EXAMPLE 3—DRCRIR Beads, Uncured

Charge fluid bed dryer (FBD) equipped with Wurster column with CRIR beads.

Prepare a coating dispersion by mixing Plasacryl T20, filtered (250 micrometer screen) Eudragit FS 30 D and water in a container for at least 60 minutes.

Coat the CRIR beads with Eudragit FS30D dispersion.

Note: In case the manufacturing process is interrupted, Syloid 244FP, quantity based on 0.43% of the theoretical yield of CRDR beads, is added to the beads and blended.

EXAMPLE 4—DRCRIR Beads, Cured

The following protocol was used to produce the methylphenidate DRCR beads.

Charge fluid bed dryer (FBD) equipped with Wurster column with CRIR beads.

Prepare a coating dispersion by mixing Plasacryl T20, filtered (250 micrometer screen) Eudragit FS 30D and water in a container for at least 60 minutes.

Coat the CRIR beads with Eudragit FS30D dispersion at product temperature of 25°±3° C. by spraying the coating dispersion.

After completion of the coating dispersion, spray rinse water at a product temperature of 25°±3° C.

Suck into the FBD, Syloid 244FP, quantity based on 0.43% of the theoretical yield of CRDR beads and blend.

Cure the beads at a product temperature of 40°±2° C. for 60 minutes.

Cool the beads to product temperature of 25°±3° C.

Screen the beads on 0.85 mm screen and remove fines if any.

Note: In case the manufacturing process is interrupted, Syloid 244FP, quantity based on 0.43% of the theoretical yield of CRDR beads, is added to the beads and blended.

EXAMPLE 5—MPH IR Distal Beads

The following protocol was used to produce the MPH IR distal beads.

Add Opadry clear YS-1-7006 to water and mix, then add methylphenidate hydrochloride and stir until a clear solution is obtained.

Charge fluid bed dryer (FBD) equipped with Wurster column with DRCRIR beads

Coat the beads at an inlet temperature of 56°±15° C. and product temperature of 37.5°±3.5° C. by spraying the solution of methylphenidate hydrochloride.

After completion of the solution, spray rinse water at a product temperature of 37.5°±3.5° C.

Allow the beads to dry at product temperature of 41°±4° C. for 5 minutes.

Cool the beads to 30°±1° C. product temperature and weigh.

Screen the beads and collect the beads passing through 1.8 mm screen and retained on 0.85 mm screen.

EXAMPLE 6—MPH IR Distal Beads Coated with Sodium Alginate Beads

The following protocol was used to produce the MPH IR distal beads coated with sodium alginate beads.

Add talc to water and mix; stir using a homogenizer until a uniform dispersion is obtained.

Add sodium alginate to water and mix, stir until a uniform dispersion is obtained.

Add the talc dispersion on the sodium alginate and mix until a uniform dispersion is obtained.

Charge fluid bed dryer (FBD) equipped with Wurster column with MPH IR distal beads.

Coat the beads at an inlet temperature of 70°±15° C. and product temperature of 50°±5° C. by spraying the solution of sodium alginate.

Allow the beads to dry at product temperature of 41°±4° C. for 5 minutes.

Cool the beads to 30°±1° C. product temperature and weigh.

Screen the beads and collect the beads passing through 1.8 mm screen and retained on 0.85 mm screen.

EXAMPLE 7—MPH IR Distal Beads (with or without Sodium Aginate) with Silicon Dioxide The following protocol was used to produce these beads.

Charge V blender with approximately half the total quantity of MPH IR Distal Beads (with or without sodium aginate).

Screen Syloid FP 244 through 20 mesh screen and add to the V blender.

Load remaining quantity of MPH IR Distal Beads (with or without sodium aginate) into the V blender.

Blend for 3 minutes.

Discharge the blend into plastic drums lined with polyethylene bags.

EXAMPLE 8—Encapsulation of MPH IR Distal Beads (with or without Sodium Aginate) with Silicon Dioxide The following equipment is used during the capsule filling process of the MPH IR Distal Beads (with or without sodium aginate) with silicon dioxide in either hard gelatin capsules (used in these Examples) or hard hypromellose (HPMC) capsules (an alternative to hard gelatin capsules):

Bosch GKF 1400 Encapsulator & Checkweigher
Metal Detector
Empty Capsule Conveying Bin EXAMPLE 9—Testing (pK Studies and Preliminary Studies on Alcohol Resistance)

The following methodology was used.

The dissolution of various formulations was performed using USP paddle method at 100 rpm in 900 ml at 37° C. of simulated gastric fluid (without enzyme) for 2 hours, 900 ml phosphate buffer pH 6.0 for 4 hours and 7th hour onwards, 900 mL of phosphate buffer pH 7.4. The samples were withdrawn at the respective time points and analysed on HPLC using UV detector. The in vitro release data is indicated as percentage dissolved based on the label content of the active tested.

The results of a bioavailability study of this formulation indicate a biphasic release profile (FIG. 5).

It can be concluded from the in vitro dissolution data and its correspondent in vivo plasma concentration that methylphenidate can be absorbed in the distal part of the GI tract. It can also be concluded that the amount and extent of methylphenidate being absorbed depends on the excipients used in the formulation.

FIG. 1 shows that 7 to 10% of the controlled release polymer might be sufficient to provide a therapeutic effect that lasts for more than 14 hours but without the desired rapid on set of action and distinctive biphasic or triphasic pattern shown in FIG. 3 or 4. However, the next study showed that increasing the amount of the controlled release polymer up to 20% as shown in FIG. 2 prolonged the extent of release of methylphenidate. Nonetheless, the higher the amount of controlled release polymer, the less the total amount of methylphenidate is absorbed. This could be due to the degradation of methylphenidate at higher pH environments, thus less amount of methylphenidate is available at distal part of the GI tract to be absorbed in systemic circulation.

Therefore, the amount of controlled release polymer needs to be adjusted accordingly to achieve the desired distinctive in vivo plasma concentration pattern. In the case of the preferred embodiments of the present invention, the longer duration of action and distinctive pattern might be achieved between 7% to 20% weight gain of the controlled release polymer, more specifically about 16% weight gain of the controlled polymer. The 16% would provide the desired total amount and extent of methylphenidate in plasma concentration over time in a distinctive pattern that differentiates this formulation from any other long acting solid dose methylphenidate formulation available in the market. Moreover, it achieves duration of action of no less than 14 hours.

Formulation I also has the property that does not undergo food effect as shown in FIG. 5 and Table 3. It can also be sprinkled on apple sauce, yogurt or ice cream for up to 10 minutes without affecting its bioavailability performance as shown in FIG. 6 and Table 5. Compared to three equivalent doses of immediate-release methylphenidate administered separately at 4 hourly intervals, Formulation I has greater residual levels of methylphenidate at hour 24 post-administration and different partial AUCs during the dosing interval, particularly in the 12-16 hour period where the pAUC is significantly larger than immediate-release methylphenidate (Table 4). In addition, the second peak of methylphenidate occurs more than 2 hours after the third peak of immediate-release methylphenidate (FIG. 5 and Table 4). As a result of the significant residual methylphenidate plasma levels at hour 24 post-administration (FIG. 5), the pharmacokinetic profile changes after multiple days of dosing resulting in an overall increase in plasma levels (FIG. 7 and Table 6) and higher peak concentrations. Formulation J has a similar pharmacokinetic profile and properties as Formulation I (FIG. 8 and Table 7).

The in vitro dissolution specifications of the drug at various time points for formulations in accordance with Formulations A-J are shown in Table 2. Based on these results and the correlation between in vivo and in vitro data, the present inventors developed the target specification should in Table 8 for preferred embodiments of the present coated bead.

Based on the studies excipients were identified and adjusted to obtain a finished product that is stable within a product shelf life of at least 24 months and provides no less than 14 hours of therapeutic effect. Stability testing of the above formulation showed that the total related substances at 6 months 40° C./75% RH are within 2.0% and no individual unknown is higher than 0.2%.

In vitro dissolution testing at 40% ethanol in SFG dissolution media was performed. As will be illustrated in Example 10, Formulation I and Formulation J were found to be resistant up to about 35% v/v and up to about 32% v/v, respectively, ethanol in SGF. Therefore, different trials were performed with immediate release excipients to be applied to the outer immediate release layer methylphenidate hydrochloride to increase the ethanol resistance to 40% ethanol v/v. Some of the excipients that were investigated individually or in combination are: sodium alginate, Kollicoat™ IR, hypromellose, Lycoat™, pectin, lactose, methylcellulose, ethylcellulose and talc. An outer layer of these excipients was applied on top of the desired methylphenidate CRDRIR formulation or formulation I/Formulation J and a test to determine in vitro alcohol resistance (see Example 10 for details of the test) was performed to determine the impact of the excipients in the formulation.

The experiment with sodium alginate in combination with talc showed that above 40% weight gain of sodium alginate the dissolution rate in 40% v/v ethanol would impart alcohol resistance to Formulation I under the prescribed test conditions. At weight gains between 55 to 75% the dissolution rate in the first two hours of the product would meet the criteria at 40% v/v ethanol and released about 20% of the IR component. Therefore, an improved CRDRIRR methylphenidate formulation (Formulation I or Formulation J) was developed. This formulation would have a most outer layer of about 55-75% weight gain of sodium alginate. This layer is applied on top of the external IR layer to provide a 40% v/v ethanol resistant formulation without affecting the original release rate of the formulation.

EXAMPLE 10—Testing (Further Studies on Alcohol Resistance)

Generally dose dumping is observed as a result of a compromise of the release-rate controlling mechanism in a pharmaceutical product. Some products can be expected to exhibit a more rapid drug dissolution and release rate in the presence of ethanol. Therefore, when a modified—release product is consumed with alcohol, the modified-release mechanism could be adversely affected, which could lead to dose dumping.

The following study was performed to evaluate the alcohol induced dose dumping in IRDR Methylphenidate HCl capsules. The effect of varying concentrations of ethanol on the drug release was evaluated at 0% (no ethanol added), 5%, 20% and 40% ethanol which are considered to be representative of consumption of beer (5% ethanol), mixed drinks (20% ethanol), and neat liquor (40% ethanol). The dissolution evaluation was also carried out in 35% ethanol to understand the effect of ethanol concentrations from 20% to 40% and at what level the alcohol induced dose dumping becomes significant.

The dissolution profiles showed that even though in the presence of 40% ethanol, the rate of dissolution rapidly increased as compared to that observed in control, the release was never considered to be dose dumping of methylphenidate HCl. Furthermore, in the presence of 35% ethanol the rate of release increased but the average percentage release amount was determined to be similar when the f2, similarity factor, was calculated against the control sample. The calculated value was 50. An f2 value of 50-100 suggests similar dissolution profiles.

The experiments were carried out on 12 units as following: The ethanolic dissolution media used were 5%, 20%, 35% and 40% USP anhydrous ethanol in 0.1N HCl (v/v). The experiments were performed in 900 ml of respective media using USP apparatus 1 (baskets) at 100 rpm and 37° C. The control (0% ethanol) was also run using 900 ml of 0.1 N HCl. The 0.1 N HCl was selected to approximate the conditions in the stomach.

The samples were collected every 15 minutes up to 2 hours to understand the release profile starting as early as 15 minutes. Since the dissolution experiments were run for 2 hours, and the vessels were covered at all times, the media evaporation had no impact on the results. The samples were analyzed on HPLC as per specified IRDR Methylphenidate HCl capsule dissolution method and the percent released methylphenidate HCl at each time point was calculated. The dissolution and HPLC parameters are reported in Table 14.

Resistance to ethanol means that the release of the pharmaceutical active ingredient is in the presence of ethanol not more than 20% to be measured under in-vitro conditions at pH 1.2 for 2 hours in 900 mL medium according to USP with the addition of 5, 10, 20 or 40% (v/v) ethanol at 100 rpm using USP. Dose Dumping is defined as unintended, rapid drug release in a short period of time of a significant amount of the drug contained in a modified release dosage form. Dose dumping shall mean that the release of the pharmaceutical active ingredient is faster but does not release more than 25%, no more than 20% to be measured under in-vitro conditions at pH 0.2 for 60 minutes in medium according to USP with the addition of 5, 10, 20 or 40% (v/v) ethanol.

In this study, the focus was on coating application as a function of theoretical weight gain of coating applied to the nonpareil beads. Since it is also common to quantify film coating amount as mass/surface area, film coating amount (mg/cm$^2$) was determined using a calculation for surface area, assuming the bead is a perfect sphere:

$$SA=4(\pi r^2)$$

wherein SA is the surface area and r is the radius of the bead.

Conventional round nonpareil beads with diameters ranging from 0.85 to 1.4 mm with an average of 1.125 mm were used in this ethanol resistance study. The surface area of beads of this average diameter was calculated as follows:

$$SA=4(\pi(0.5625^2))$$

$$SA=3.98 \text{ mm}^2$$

Conventional round nonpareil beads with diameters ranging from 0.85 to 1.4 mm with an average of 1.125 mm were used in this ethanol resistance study.

Since a certain layer thickness is desirable in film coating with Eudragit FS30D to impart alcohol resistant properties up to 30%, up to 32%, up to 35% without the capsules possessing dose dumping characteristics of the active pharmaceutical ingredient within the first 60 minutes; the amount of coating material is related to the surface area of the substrate per cm$^2$ of surface area. Thus, the inventors divided the surface area of a substrate A (mm$^2$) by its weight gain w (mg), to obtain the desired coating quantity in % (w/w), i.e. as shown in the following equation:

$$\text{Coating weight } (\%)=[A \text{ (mm}^2)/w \text{ (mg)}]*1 \text{ (mg/cm}^2)$$

The total amount of the delayed (or distal) release (e.g., colonic delivery) material may be in the range of from about 5% to about 35% by weight, preferably from about 10% to 30% by weight, most preferably from about 15 to about 25% by weight, in relation to the weight of the core.

The absolute amount of the delayed (or distal) release (e.g., colonic delivery) material described above (prior to the examples) may, in the case of pellets or granules with a diameter size in the range of from about 840 to 1410 μm, be present at an average thickness in the range in from about 5 μm to about 50 μm, preferably from about 10 μm to about 50 μm, more preferably from about 33 μm to about 47 μm, most preferably about 40 μm.

It can be preferred to use poly(methyl acrylate-co-methyl methacrylate-co-methacrylic acid) 7:3:1 as the delayed (or distal) release (e.g., colonic delivery) material. Such a material is commercially available from Evonik under the tradement name Eudragit® FS30D.

The presence of ethanol in concentrations of 5, 10, 20 or 40% (volume/volume) in the gastric fluid usually leads to an increase to the release rates in the stomach. Due to distribution effect the effect of ingested ethanol is in the intestine not of that importance as in the stomach. Thus an effective protection against the influence of ethanol should prevent such an undesired increase of pharmaceutical active ingredient in the stomach in the first place. Furthermore it may be desired that protection against the influence of ethanol shall at least not influence the comparably fast release rates at pH 6.8 in media without ethanol.

International Patent Publication WO 2012/0224998 describes a gastric resistant pharmaceutical or nutraceutical composition, comprising a core, comprising a pharmaceutical or nutraceutical active ingredient and a gastric resistant coating layer onto the core, wherein the release of the pharmaceutical active ingredient is not more than 15% under in-vitro conditions at pH 1.2 for 2 hours in a buffered medium according to USP with and without the addition of 40% (v/v) ethanol, wherein the gastric resistant coating layer comprises 10 to 100% by weight of one or more salts of alginic acid with a viscosity of 30 to 720 cP of a 1% aqueous solution. The one layer system as described is stated to solve the problem of protection against the influence of ethanol. However, there is no reference of ethanol protection provided by coating layer containing Eudragit™ FS30D at any ethanol concentration by itself or when the coatings which include the ammonium alginate, coatings which employ other alginate salts, like sodium or potassium alginate, are deposited in the most outer layer of the bead.

The data demonstrated that the in-vitro rate of dissolution of methylphenidate HCl did not increase in the presence of 5% and 20% ethanol within two hours as compared to that in control; and the in-vitro rate of dissolution of methylphenidate HCl did not increase in the presence of 5%, 20%, 35% and 40% ethanol within 30 minutes as compared to that in control. Nevertheless, in the presence of 35% and 40% ethanol, more rapid increase was observed in the dissolution release rate after 30 minutes. Even though a faster release was observed, the release of the active pharmaceutical ingredients was still in a controlled release manner. Dose dumping of methylphenidate hydrochloride did not occur at any time of the release in presence of different concentration of ethanol up to 40%.

The results of this study are believed to be a reasonable basis for the present inventors to predict similar resistance to alcohol (e.g., ethanol) would be observed clinically and for active ingredients other than methylphenidate HCl.

EXAMPLE 11—a Randomized, Double-Blind Study of the Time Course of Response of MPH-IR Distal Bead (Formulation I) in Adult with ADHD in a Simulated Adult Workplace Environment (AWE)

Objectives

The purpose of this randomized, double-blind, crossover, placebo-controlled, optimized-dose study was to assess the clinical efficacy, time of onset and time course of efficacy over 16 hours of MPH-IR Distal Bead compared to placebo in adults diagnosed with ADHD in an AWE setting.

Methodology

This study (063-008) was a randomized, double-blind, placebo-controlled cross-over study in adult, male and female ADHD subjects conducted to assess clinical efficacy, the time of onset and time course of efficacy of MPH-IR Distal Bead measured by the Permanent Product Measure of Performance (PERMP) (an objective, skill-adjusted math test that measures attention in ADHD) score. Subjects were titrated to an optimal dose in an open-label phase of between 2 and 7 weeks, familiarized with study procedures in a practice AWE session and then randomized to one of two sequences (ACTIVE to PLACEBO or PLACEBO to ACTIVE) and received one treatment for one week, followed by an AWE session, then crossed over to the other treatment for one week, followed by a second AWE session.

Number of Subjects

Planned: 60 subjects. Randomised: 59 subjects. Completed: 46 subjects.

Test Treatment, Dose, and Mode of Administration

Active or matching placebo MPH-IR Distal Bead (methylphenidate hydrochloride controlled-release—Formulation I in Table 1) 25, 35, 45, 55, 70, 85 or 100 mg oral capsules were administered once-daily in the morning.

Duration of Treatment

Subjects received open label medication during a 2 to 9 week dose titration, followed by a double-blind crossover of one week of placebo treatment and one week of active treatment.

Criteria for Evaluation

The primary outcome measure was the mean between-treatment PERMP Total score across the AWE sessions. Secondary outcome measures included the onset and time course of efficacy of MPH-IR Distal Bead compared to placebo as measured by the PERMP Total Score (PERMP-T), PERMP Attempted Score (PERMP-A) and PERMP Correct Score (PERMP-C) at pre-dose and 1.0, 2.0, 5.0, 8.0, 11.0, 14.0 and 16.0 hours post-dose and the onset and time course of efficacy of MPH-IR Distal Bead compared to placebo as measured by the SKAMP (a subjective measure of behaviour), using the combined score (SKAMP-C), the SKAMP-Deportment (SKAMP-D) subscale and SKAMP Attention (SKAMP-A) subscale at pre-dose and 0.5, 1.0, 2.0, 4.0, 5.0, 7.0, 8.0, 11.0, 13.0, 14.0 and 16.0 hours post-dose.

Efficacy & Safety Results

The study met the primary endpoint in that subjects treated with MPH-IR Distal Bead had improved attention compared to subjects receiving placebo, as measured by the mean change from pre-dose PERMP-Total Scores (FIG. 9).

Subjects receiving MPH-IR Distal Bead showed improvement in attention with an onset of action within 1.0 hour of receiving active medication compared to placebo with duration of effect continuing for up to and including 16.0 hours post-dose, based on change from pre-dose LS mean difference from placebo PERMP-Total Scores (FIG. 9).

Figure 10:
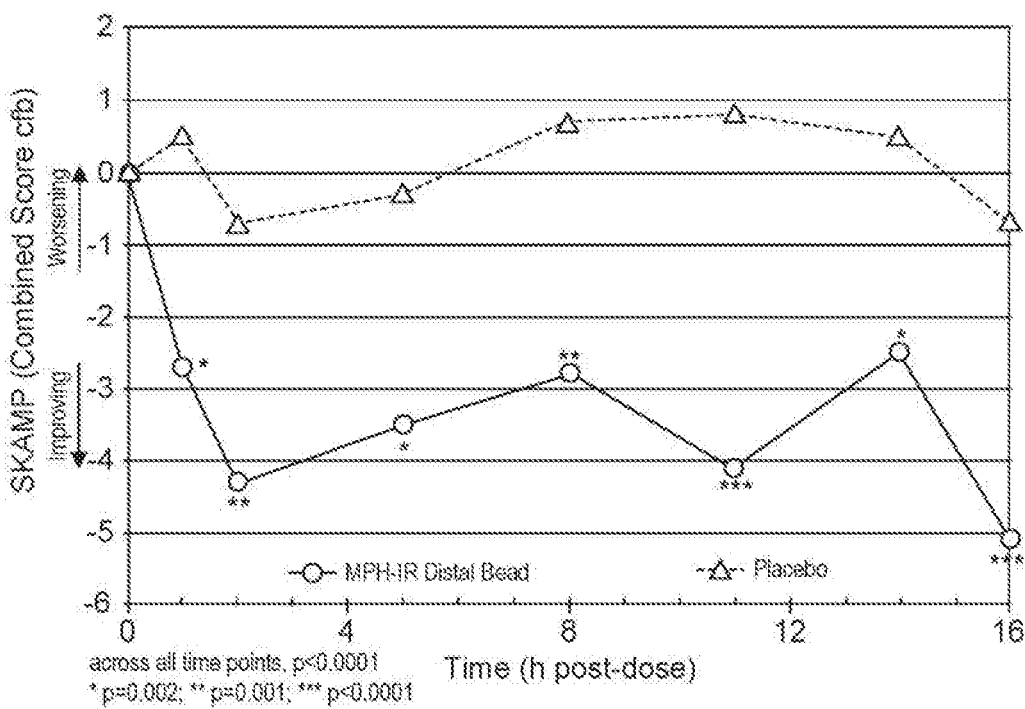

Subjects receiving MPH-IR Distal Bead showed improvement in behaviour with an onset of action within 1.0 hour of receiving active medication compared to placebo with duration of effect continuing for up to and including 16.0 hours post-dose based on change from pre-dose LS mean difference from placebo SKAMP-C Scores (FIG. 10).

MPH-IR Distal Bead was relatively safe and well-tolerated medication.

Overall Conclusions

MPH-IR Distal Bead was safe and effective in the treatment of adults with ADHD, demonstrating efficacy from one hour to 16 hours post administration on both objective and subjective measures. Subjects demonstrated significant improvement in the primary endpoint—an objective measure of attention (the PERMP)—and the secondary endpoint—a subjective measure of behaviour (the SKAMP)—during the double-blind phase of the study when treated with MPH-IR Distal Bead compared to when treated with placebo.

In addition, the study medication was well-tolerated, with no serious adverse events. Patients reported satisfaction with ability to fall asleep, appetite for lunch, appetite for dinner or overall adverse effects and no significant differences compared to placebo in sleep quality.

The onset and duration of action at one hour and 16 hours post-administration respectively, is the result of the pharmacokinetic profile of MPH-IR Distal Bead. The residual methylphenidate plasma concentration at hour 24 post-administration leads to an increase in the first peak of methylphenidate following multiple days of dosing, resulting in an onset of action with one hour. In addition, the second peak of methylphenidate is also increased following multiple days of dosing, providing sufficient plasma levels of methylphenidate late in the day that results in a prolonged duration of action extending to 16 hours post-administration. The pharmacokinetic profile of this formulation provides a combination of rapid onset and a prolonged duration of action in a single daily administration.

EXAMPLE 12—Preferred Formulations

Based on the exemplary work described above, Formulations I and J were identified as the most preferred for the present coated bead. Tables 15 and 16 provide complete formulation specifications for oral solid pharmaceutical composition based on Formulations I and J, respectively for the following dosage strengths of methylphenidate HCl: 25 mg, 30, mg, 35 mg, 45 mg, 55 mg, 70 mg, 85 mg and 100 mg.

While this invention has been described with reference to illustrative embodiments and examples, the description is not intended to be construed in a limiting sense. Thus, various modifications of the illustrative embodiments, as well as other embodiments of the invention, will be apparent to persons skilled in the art upon reference to this description. It is therefore contemplated that the appended claims will cover any such modifications or embodiments.

All publications, patents and patent applications referred to herein are incorporated by reference in their entirety to the same extent as if each individual publication, patent or patent application was specifically and individually indicated to be incorporated by reference in its entirety.

TABLE 1

| | Strength (label claim) 20 mg | | | | Strength (label claim) 20 mg | | | |
|---|---|---|---|---|---|---|---|---|
| | Formulation A - 7% 063-001 DRCRIR bead | | Formulation B - 10% 063-001 DRCRIR bead | | Formulation C - 16% 063-002 DRCRIR bead | | Formulation D - 20% 063-002 DRCRIR bead | |
| Ingredient | Quantity per unit | % | Quantity per unit | % | Quantity per unit | % | Quantity per unit | % |
| Methylphenidate HCl, USP | 20.0 | 11.25 | 20.0 | 10.88 | 20.0 | 10.19 | 20.0 | 9.79 |
| Sugar spheres 14/18 mesh, USP/NF | 107.0 | 60.2 | 107.0 | 58.2 | 107.0 | 54.5 | 106.8 | 52.3 |
| Opadry Clear YS-1-7006, USP | 6.4 | 3.6 | 6.4 | 3.5 | 6.5 | 3.3 | 6.4 | 3.1 |
| Ammonio methacrylate copolymer dispersion, Type B, 30% dispersion (Eudragit RS30D Solids), NF | 9.4 | 5.26 | 13.3 | 7.24 | 21.3 | 10.86 | 26.7 | 13.05 |
| Triethyl Citrate, USP/NF | 1.4 | 0.80 | 2.0 | 1.10 | 3.3 | 1.67 | 4.1 | 2.00 |
| Glyceryl monostearate emulsion (Plasacryl T20), HS | 3.8 | 2.18 | 4.3 | 2.37 | 5.3 | 2.74 | 6.0 | 2.94 |
| Silicon dioxide, (Syloid 244FP), NF | 0.7 | 0.4 | 0.7 | 0.4 | 0.8 | 0.4 | 0.8 | 0.4 |
| Eudragit FS30D Liquid, HS | 29.0 | 16.32 | 30.0 | 16.32 | 32.0 | 16.32 | 33.3 | 16.32 |
| Total weigh in capsule (mg) | ~178 | ~100 | ~184 | ~100 | ~196 | ~100 | ~204 | ~100 |

| | Strength (label claim) 30 mg Formulation E - 70:30 063-002 ECCRIR bead (70%) + DRCRIR bead (30%) | Strength (label claim) 30 mg Formulation F - 80:20 063-003 DRCRIR bead (80%) + IR bead (20%) |
|---|---|---|
| Ingredient | Quantity per unit (%) | Quantity per unit (%) |
| 1. IR bead | IR bead (0%) | IR bead (20%) |
| Methylphenidate HCl, USP | — | 15.0 |
| Sugar spheres 14/18 mesh, USP/NF | — | 80.2 |
| Opadry Clear YS-1-7006, USP | — | 4.8 |
| Total IR bead | — | ~100% |
| 7. CR/EC/IR bead | ECCRIR bead (70%) | ECCRIR bead (0%) |
| Methylphenidate HCl, USP | 12.78 | — |
| Sugar spheres 14/18 mesh, USP/NF | 62.02 | — |
| Opadry Clear YS-1-7006, USP | 4.04 | — |
| Ammonio methacrylate copolymer dispersion, Type B, 30% dispersion (Eudragit RS30D Solids), NF | 5.44 | — |
| Methacrylic Acid copolymer dispersion, 30% dispersion (Eudragit L30 D-55 solids), USP NF | 8.15 | — |

TABLE 1-continued

| Ingredient | | |
|---|---|---|
| Triethyl Citrate, USP/NF | 2.70 | — |
| Talc Ph. Eur/USP | 4.87 | — |
| Total CR/EC/IR bead | ~100% | ~100% |
| 6. CR/DR bead | DRCRIR bead (30%) | DRCRIR bead (80%) |
| Methylphenidate HCl, USP | 10.19 | 10.19 |
| Sugar spheres ¹⁴/₁₈ mesh, USP/NF | 54.5 | 54.5 |
| Opadry Clear YS-1-7006, USP | 3.3 | 3.3 |
| Ammonio methacrylate copolymer dispersion, Type B, 30% dispersion (Eudragit RS30D Solids), NF | 10.86 | 10.86 |
| Triethyl Citrate, USP/NF | 1.67 | 1.67 |
| Glyceryl monostearate emulsion (Plasacryl T20), HS | 2.74 | 2.74 |
| Silicon dioxide, (Syloid 244FP), NF | 0.4 | 0.4 |
| Eudragit FS30D Liquid, HS | 16.32 | 16.32 |
| Total CR/DR bead (30%) | ~100% | ~100% |
| Total weight in capsule | ~211 mg | ~275 mg |

| Ingredient | Strength (label claim) 30 mg Formulation G - 30:55:15 063-003 ECCRIR bead (30%) + DRCRIR bead (55%) + IR bead (15%) Quantity per unit (%) | Strength (label claim) 30 mg Formulation H - 35:55:10 063-003 ECCRIR bead (35%) + DRCRIR bead (55%) + IR bead (10%) Quantity per unit (%) |
|---|---|---|
| 1. IR bead | IR bead (15%) | IR bead (10%) |
| Methylphenidate HCl, USP | 15.0 | 15.0 |
| Sugar spheres ¹⁴/₁₈ mesh, USP/NF | 80.2 | 80.2 |
| Opadry Clear YS-1-7006, USP | 4.8 | 4.8 |
| Total IR bead | ~100% | ~100% |
| 7. CR/EC/IR bead | ECCRIR bead (30%) | ECCRIR bead (35%) |
| Methylphenidate HCl, USP | 12.78 | 12.78 |
| Sugar spheres ¹⁴/₁₈ mesh, USP/NF | 62.02 | 62.02 |
| Opadry Clear YS-1-7006, USP | 4.04 | 4.04 |
| Ammonio methacrylate copolymer dispersion, Type B, 30% dispersion (Eudragit RS30D Solids), NF | 5.44 | 5.44 |
| Methacrylic Acid copolymer dispersion, 30% dispersion (Eudragit L30 D-55 solids), USP NF | 8.15 | 8.15 |
| Triethyl Citrate, USP/NF | 2.70 | 2.70 |
| Talc Ph. Eur/USP | 4.87 | 4.87 |
| Total CR/EC/IR bead | ~100% | ~100% |
| 6. CR/DR bead | DRCRIR bead (55%) | DRCRIR bead (55%) |
| Methylphenidate HCl, USP | 10.19 | 10.19 |
| Sugar spheres ¹⁴/₁₈ mesh, USP/NF | 54.5 | 54.5 |
| Opadry Clear YS-1-7006, USP | 3.3 | 3.3 |
| Ammonio methacrylate copolymer dispersion, Type B, 30% dispersion (Eudragit RS30D Solids), NF | 10.86 | 10.86 |
| Triethyl Citrate, USP/NF | 1.67 | 1.67 |
| Glyceryl monostearate emulsion (Plasacryl T20), HS | 2.74 | 2.74 |
| Silicon dioxide, (Syloid 244FP), NF | 0.4 | 0.4 |
| Eudragit FS30D Liquid, HS | 16.32 | 16.32 |
| Total CR/DR bead (30%) | ~100% | ~100% |
| Total weight in capsule | ~262 mg | ~264 mg |

| Ingredient | Strength (label claim) 100 mg Formulation F 80:20 063-003 DRCRIR bead + IR bead Quantity per unit (%) | Strength (label claim) 100 mg Formulation I 80:20 063-004, 063-005, 063-007 063-008 MPH IR distal bead Quantity per unit (%) | Strength (label claim) 100 mg Formulation J 80:20 063-011 MPH IR distal bead Quantity per unit (%) |
|---|---|---|---|
| 1. IR bead | IR bead (20%) | IR bead (0%) | IR bead (0%) |
| Methylphenidate HCl, USP | 15.0 | — | — |
| Sugar spheres ¹⁴/₁₈ mesh, USP/NF | 80.2 | — | — |
| Opadry Clear YS-1-7006, USP | 4.8 | — | — |
| Total IR bead | ~100% | — | — |

TABLE 1-continued

| 6. CR/DR bead | DRCRIR bead (80%) | DRCRIR bead (0%) | DRCRIR bead (0%) |
|---|---|---|---|
| Methylphenidate HCl, USP | 10.19 | — | — |
| Sugar spheres 14/18 mesh, USP/NF | 54.5 | — | — |
| Opadry Clear YS-1-7006, USP | 3.3 | — | — |
| Ammonio methacrylate copolymer dispersion, Type B, 30% dispersion (Eudragit RS30D Solids), NF | 10.86 | — | — |
| Triethyl Citrate, USP/NF | 1.67 | — | — |
| Glyceryl monostearate emulsion (Plasacryl T20), HS | 2.74 | — | — |
| Silicon dioxide, (Syloid 244FP), NF | 0.4 | — | — |
| Eudragit FS30D Liquid, HS | 16.32 | — | — |
| Total CR/DR bead | ~100% | — | — |

| 8. CR/DR/IR bead | MPH IR distal bead | MPH IR distal bead Quantity per unit (mg) | % | MPH IR distal bead Quantity per unit (mg) | % |
|---|---|---|---|---|---|
| Methylphenidate HCl, USP | — | 100 | 12.3 | 100 | 18.4 |
| Sugar spheres 14/18 mesh or 18/20 mesh, USP/NF | — | 428.5 | 52.7 | 243.1 | 44.7 |
| Opadry Clear YS-1-7006, USP | — | 31.7 | 3.9 | 32.2 | 5.9 |
| Ammonio methacrylate copolymer dispersion, Type B, 30% dispersion (Eudragit RS30D Solids), NF | — | 85.4 | 10.5 | 55.55 | 10.3 |
| Triethyl Citrate, USP/NF | — | 13.0 | 1.6 | 8.61 | 1.6 |
| Glyceryl monostearate emulsion (Plasacryl T20), HS | — | 22.0 | 2.7 | 14.1 | 2.6 |
| Silicon dioxide, (Syloid 244FP), NF | — | 4.1 | 0.5 | 4.52 | 0.8 |
| Eudragit FS30D Liquid, HS | — | 128.5 | 15.8 | 84.61 | 15.6 |
| Total weight in capsule | ~1100 mg | ~813 mg | ~100% | ~543 mg | ~100% |

TABLE 2

Dissolution results

% Methylphenidate HCl dissolved

| Dissolution | Time (hours) | Formulation A | Formulation B | Formulation C | Formulation D | Formulation E | Formulation F | Formulation G | Formulation H | Formulation I | Formulation J |
|---|---|---|---|---|---|---|---|---|---|---|---|
| USP paddle method, 100 rpm, at 37° C., 900 ml simulated gastric fluid for 2 hours, 900 ml phosphate buffer pH 6.0 for 4 hours and 7th hour onwards, 900 mL of phosphate buffer pH 7.4 USP<711>Acceptance Table 2 | 1 | 4 | 4 | 1 | 1 | 25 | 18 | 25 | 24 | 20 | 20 |
| | 4 | 11 | 10 | 3 | 4 | 31 | 22 | 29 | 28 | 21 | 21 |
| | 8 | 41 | 49 | 28 | 38 | 54 | 46 | 61 | 61 | 44 | 41 |
| | 12 | 68 | 76 | 44 | 40 | 64 | 58 | 71 | 71 | 83 | 73 |
| | 16[1] | 79 | 78 | 54 | 41 | 68 | 67 | 74 | 73 | 78 | 79 |

[1] The total amount of Methylphenidate HCl decreases as it degrades at pH 7.4.

TABLE 3

Ratios, 90% Geometric CI for non-dose-normalized Parameters Study 063-004

| Parameter | Treatment Comparisons | Ratio | 90% Geometric C.I. Lower | 90% Geometric C.I. Upper |
|---|---|---|---|---|
| $AUC_{0-t}$ | Formulation I (fed) vs IR-MPH (fed) | 102.73% | 97.69% | 108.03% |
| | Formulation I (fast) vs IR-MPH (fast) | 123.92% | 117.87% | 130.29% |
| | Formulation I (fed) vs (fast) | 98.02% | 93.21% | 103.07% |
| $AUC_{0-inf}$ | Formulation I (fed) vs IR-MPH (fed) | 128.07% | 122.18% | 134.24% |
| | Formulation I (fast) vs IR-MPH (fast) | 147.91% | 141.31% | 154.83% |
| | Formulation I (fed) vs (fast) | 102.09% | 97.41% | 107.01% |

TABLE 3-continued

Ratios, 90% Geometric CI for non-dose-normalized Parameters Study 063-004

| Parameter | Treatment Comparisons | Ratio | 90% Geometric C.I. Lower | 90% Geometric C.I. Upper |
|---|---|---|---|---|
| $C_{max}$ | Formulation I (fed) vs IR-MPH (fed) | 71.17% | 65.92% | 76.83% |
| | Formulation I (fast) vs IR-MPH (fast) | 87.06% | 80.66% | 93.96% |
| | Formulation I (fed) vs (fast) | 89.31% | 82.73% | 96.41% |

TABLE 5

Ratios, 90% Geometric CI for non-dose-normalized Parameters Study 063-005

| Parameter | Treatment Comparisons | Ratio | 90% Geometric C.I. Lower | 90% Geometric C.I. Upper |
|---|---|---|---|---|
| AUC0-t | Test(A) - Reference(D) | 98.78% | 95.30% | 102.40% |
| | Test(B) - Reference(D) | 98.60% | 95.11% | 102.22% |
| | Test(C) - Reference(D) | 101.08% | 97.52% | 104.78% |
| AUC0-inf | Test(A) - Reference(D) | 97.87% | 94.45% | 101.41% |
| | Test(B) - Reference(D) | 98.45% | 95.01% | 102.02% |
| | Test(C) - Reference(D) | 101.35% | 97.82% | 105.01% |
| Cmax | Test(A) - Reference(D) | 108.31% | 100.05% | 117.26% |
| | Test(B) - Reference(D) | 100.08% | 92.43% | 108.37% |
| | Test(C) - Reference(D) | 105.84% | 97.77% | 114.57% |

TABLE 6

Ratios, 90% Geometric CI for non-dose-normalized Parameters Study 063-007

| Parameter | Treatment Comparisons | Ratio | 90% Geometric C.I. Lower | 90% Geometric C.I. Upper |
|---|---|---|---|---|
| $AUC_{0-24}$ | Formulation I vs IR-MPH | 147.61% | 143.02% | 152.34% |
| $C_{max}$ | Formulation I vs IR-MPH | 98.92% | 92.48% | 105.81% |
| $C_{min}$ | Formulation I vs IR-MPH | 456.91% | 404.67% | 515.90% |

TABLE 4

Summary of non-dose-normalized Pharmacokinetic Results Study 063-004

| | Formulation I (100 mg Fast) | Formulation I (100 mg Fed) | Ritalin (20 mg x 3 Fast) | Ritalin (20 mg x 3 Fed) |
|---|---|---|---|---|
| $AUC_{0-t}$ (pg · hr/mL) | 167783.86 ± 46487.66 | 161271.48 ± 40500.38 | 132957.12 ± 43955.82 | 155290.78 ± 37540.22 |
| $AUC_{0-inf}$ (pg · hr/mL) | 205610.43 ± 61472.88 | 202964.28 ± 57449.88 | 136436.27 ± 45902.96 | 159381.72 ± 39469.43 |
| Residual Area (%) | 17.62 ± 11.06 | 18.63 ± 8.51 | 2.42 ± 0.96 | 2.45 ± 0.92 |
| $C_{max}$ (pg/mL) | 12875.81 ± 4590.85 | 11088.11 ± 2699.06 | 14105.39 ± 3770.36 | 15247.79 ± 3288.76 |
| $T_{max}$ (hr) | 11.5 | 12.5 | 9.50 | 6.04 |
| $K_{el}$ (1/hr) | 0.1173 ± 0.0430 | 0.1074 ± 0.0296 | 0.1968 ± 0.0218 | 0.1976 ± 0.0247 |
| $T_{1/2\,el}$ (hr) | 6.95 ± 3.25 | 7.03 ± 2.28 | 3.57 ± 0.40 | 3.56 ± 0.45 |
| $AUC_{0-4}$ (pg · hr/mL) | 24818.34 ± 7976.76 | 21160.21 ± 6420.56 | 22955.21 ± 8292.78 | 26886.10 ± 7606.67 |
| $AUC_{8-12}$ (pg · hr/mL) | 36457.19 ± 18489.84 | 29392.15 ± 8453.72 | 41094.69 ± 12181.51 | 44914.86 ± 8753.20 |
| $AUC_{12-16}$ (pg · hr/mL) | 39322.95 ± 10236.29 | 36653.88 ± 11521.14 | 20364.91 ± 9558.52 | 24467.89 ± 8948.65 |
| $AUC_{0-8}$ (pg · hr/mL) | 48626.93 ± 16709.44 | 47422.42 ± 9947.71 | 58725.69 ± 17067.12 | 70056.85 ± 16031.58 |
| $AUC_{0-12}$ (pg · hr/mL) | 85084.12 ± 33395.48 | 76814.57 ± 16722.84 | 99820.38 ± 28132.26 | 114971.70 ± 23607.37 |
| $AUC_{0-16}$ (pg · hr/mL) | 124407.07 ± 40902.66 | 113468.45 ± 26835.93 | 120185.29 ± 37077.85 | 139439.59 ± 30402.02 |
| $AUC_{0-24}$ (pg · hr/mL) | 167740.82 ± 46495.35 | 161217.02 ± 40475.17 | 132949.12 ± 43953.43 | 155281.82 ± 37538.47 |
| $AUC_{4-8}$ (pg · hr/mL) | 23500.00 ± 10293.79 | 25814.81 ± 6376.73 | 35446.96 ± 9454.91 | 42739.42 ± 10194.06 |
| $AUC_{12-t}$ (pg · hr/mL) | 82699.74 ± 21862.39 | 84456.90 ± 26718.88 | 33136.74 ± 16892.19 | 40319.08 ± 17657.25 |
| $C_{max0-4}$ (pg/mL) | 9365.42 ± 3213.96 | 9248.95 ± 1886.65 | 9206.46 ± 3371.78 | 10951.60 ± 3222.66 |
| $C_{max4-8}$ (pg/mL) | 7927.79 ± 4347.57 | 8162.71 ± 1932.67 | 12684.06 ± 3583.22 | 14454.13 ± 3450.37 |
| $C_{max8-16}$ (pg/mL) | 12413.97 ± 4546.66 | 10667.64 ± 3017.29 | 13650.77 ± 3689.34 | 14174.43 ± 3158.31 |
| $T_{max0-4}$ (hr) | 1.63 | 3.00 | 2.00 | 2.07 |
| $T_{max4-8}$ (hr) | 4.00 | 3.95 | 6.00 | 6.00 |
| $T_{max8-16}$ (hr) | 12.5 | 13.5 | 9.52 | 10.0 |

TABLE 7

Ratios, 90% Geometric CI Parameters for Study 063-011

| Parameter | Treatment Comparisons | Ratio | 90% Geometric C.I. Lower | 90% Geometric C.I. Upper |
|---|---|---|---|---|
| $AUC_{0-t}$ | Formulation I vs Formulation J (fed) | 99.15% | 91.82% | 107.08% |
| | Formulation I vs Formulation J (fast) | 99.64% | 92.27% | 107.61% |
| $AUC_{0-inf}$ | Formulation I vs Formulation J (fed) | 98.66% | 91.67% | 106.20% |
| | Formulation I vs Formulation J (fast) | 98.76% | 91.75% | 106.29% |
| $C_{max}$ | Formulation I vs Formulation J (fed) | 98.34% | 83.67% | 115.60% |
| | Formulation I vs Formulation J (fast) | 90.87% | 77.31% | 106.81% |

TABLE 8

| Time (hours) | % Methylphenidate HCl dissolved |
|---|---|
| 1 | NLT 15% |
| 4 | 18-38% |
| 8 | 35-55% |
| 12 | 68-98 |
| 16 | NLT 68 |

TABLE 9

Production of Methylphenidate Immediate Release (IR) Beads

| Process Parameters Coating sugar spheres with methylphenidate solution | Recommended Parameters Preheating | Recommended Parameters Fluid bed coating |
|---|---|---|
| Inlet air volume, cmh (to be adjusted as necessary) | 800 ± 300 | 1100 ± 200 |
| Inlet air temperature, ° C. | 56 ± 5 | 65 ± 10 |
| Atomization air pressure, bar | 1 ± 0.2 | 3 ± 1 |
| Inlet dew point, ° C. | 8 ± 4 | 8 ± 4 |
| Product temperature, ° C. | 35 ± 2 | 37.5 ± 3.5 |
| Spraying rate, g/min (to be adjusted as necessary) | N/A | 150-400 |

TABLE 9-continued

Production of Methylphenidate Immediate Release (IR) Beads

| Rinsing with purified water | Rinsing | Drying | Cooling |
|---|---|---|---|
| Amount of water used (kg) | 1 | N/A | N/A |
| Fluidized air volume, cmh (to be adjusted as necessary) | 1100 ± 200 | 1000 ± 200 | 1000 ± 300 |
| Inlet air temperature, ° C. (to be adjusted as necessary) | 65 ± 10 | 60 ± 6 | Minimum |
| Atomization air pressure, bar | 3 ± 1 | 1 ± 0.2 | 1 ± 0.2 |
| Inlet dew point, ° C. | 8 ± 4 | 8 ± 4 | 8 ± 4 |
| Product temperature, ° C. | 36 ± 3 | 41 ± 4 | 30 ± 1 |
| Spraying rate, g/min (to be adjusted as necessary) | 150-350 | N/A | N/A |
| Time, min | N/A | ~3 | N/A |

TABLE 10

Production of Methylphenidate Controlled Release (CRIR) Beads

| Process Parameters Coating IR beads with Controlled Release coating dispersion | Recommended Parameters Preheating | Recommended Parameters CR Coating | Recommended Parameters Rinsing |
|---|---|---|---|
| Amount of purified water used (Kg) | N/A | N/A | 1 |
| Inlet air volume, cmh (to be adjusted as necessary) | 1000 ± 250 | 1250 ± 350 | 1250 ± 250 |
| Inlet air temperature, ° C. | 45 ± 5 | 45 ± 15 | 45 ± 15 |
| Atomization air pressure, bar | 1 ± 0.2 | 2.8 ± 0.5 | 2.8 ± 0.5 |
| Inlet dew point, ° C. | 8 ± 4 | 8 ± 4 | 8 ± 4 |
| Product temperature, ° C. | 25 ± 3 | 25 ± 5 | 25 ± 5 |
| Spraying rate, g/min (to be adjusted as necessary) | N/A | 100-400 | 100-350 |

TABLE 11

Production of Methylphenidate Distal (DRCRIR) Beads, cured

| Process Parameters Coating CRIR beads with Distal Release coating dispersion | Recommended Parameters DR Coating | Recommended Parameters Rinsing | Recommended Parameters Curing | Recommended Parameters Cooling |
|---|---|---|---|---|
| Amount of purified water used (Kg) | N/A | 1 | N/A | N/A |
| Inlet air volume, cmh (to be adjusted as necessary) | 1400 ± 400 | 1400 ± 400 | 800 ± 400 | 800 ± 100 |
| Inlet air temperature, ° C. | 45 ± 15 | 45 ± 15 | To be adjusted | 15 ± 10 |
| Atomization air pressure, bar | 2.8 ± 0.5 | 2.8 ± 0.5 | 1 ± 0.2 | 1 ± 0.2 |
| Inlet dew point, ° C. | 8 ± 4 | 8 ± 4 | 8 ± 4 | 8 ± 4 |
| Product temperature, ° C. | 25 ± 3 | 25 ± 3 | 40 ± 2 | 25 ± 3 |
| Spraying rate, g/min (to be adjusted as necessary) | 150-400 | 150-350 | N/A | N/A |
| Time, min. | N/A | N/A | 60 | N/A |

TABLE 12

Production of Methylphenidate IR Distal (MPH IR distal) Beads

| Process Parameters Coating DRCRIR beads with Immediate Release layer | Recommended Parameters | | | | |
|---|---|---|---|---|---|
| | Preheating | IR coating | Rinsing | Drying | Cooling |
| Amount of purified water used (Kg) | N/A | N/A | 1 | N/A | N/A |
| Inlet air volume, cmh (to be adjusted as necessary) | 1100 ± 400 | 1400 ± 400 | 1400 ± 400 | 1100 ± 400 | 1100 ± 400 |
| Inlet air temperature, ° C. | 56 ± 15 | 56 ± 15 | 56 ± 15 | To be adjusted | 20 ± 10 |
| Atomization air pressure, bar | 3 ± 0.5 | 3 ± 0.5 | 3 ± 0.5 | 1 ± 0.2 | 1 ± 0.2 |
| Inlet dew point, ° C. | 8 ± 4 | 8 ± 4 | 8 ± 4 | 8 ± 4 | 8 ± 4 |
| Product temperature, ° C. | 36 ± 3 | 37.5 ± 3.5 | 37.5 ± 3.5 | 41 ± 4 | 30 ± 1 |
| Spraying rate, g/min (to be adjusted as necessary) | N/A | 150-400 | 150-350 | N/A | N/A |
| Time, min. | 5-10 | N/A | N/A | 5 | N/A |

TABLE 13

Production of Methylphenidate IR (MPH IR distal) Beads coated with Sodium Alginate

| Process Parameters Coating MPH IR distal beads with sodium alginate layer | Recommended Parameters | | | |
|---|---|---|---|---|
| | Preheating | Sodium Alginate coating | Drying | Cooling |
| Amount of purified water used (Kg) | N/A | N/A | N/A | N/A |
| Inlet air volume, cmh (to be adjusted as necessary) | 1100 ± 400 | 1400 ± 400 | 1100 ± 400 | 1100 ± 400 |
| Inlet air temperature, ° C. | 70 ± 15 | 70 ± 15 | To be adjusted | 20 ± 10 |
| Atomization air pressure, bar | 3 ± 0.5 | 3 ± 0.5 | 1 ± 0.2 | 1 ± 0.2 |
| Inlet dew point, ° C. | 8 ± 4 | 8 ± 4 | 8 ± 4 | 8 ± 4 |
| Product temperature, ° C. | 52 ± 5 | 52 ± 5 | 41 ± 4 | 30 ± 1 |
| Spraying rate, g/min (to be adjusted as necessary) | N/A | 50-300 | N/A | N/A |
| Time, min. | 5-10 | N/A | 5 | N/A |

TABLE 14

Dissolution Parameters (Example 10)

| Equipment | Conditions |
|---|---|
| Apparatus Basket, USP | apparatus 1 |
| Speed | 100 rpm |
| Bath | temperature: 37° C. |
| Dissolution media 900 ml | 0%, 5%, 20%, 35% or 40% ethanol v/v in 0.1N HCl |
| Sampling time points | 15, 30, 45, 60, 75, 90, 105, 120 minutes |

TABLE 15

Composition of the dosage form (Formulation I 80:20) MPH IR distal:

| Ingredient | Quantity per capsule (mg) per Strength (label claim) approx: | | | | | | | | |
|---|---|---|---|---|---|---|---|---|---|
| | 25 mg | 30 mg | 35 mg | 45 mg | 55 mg | 70 mg | 85 mg | 100 mg | % |
| Methylphenidate HCl, USP | 25 | 30 | 35 | 45 | 55 | 70 | 85 | 100 | 12.3 |
| Sugar spheres 14/18 mesh, USP/NF | 107.1 | 128.5 | 150.0 | 192.5 | 235.7 | 299.9 | 364.2 | 428.5 | 52.7 |
| Opadry Clear YS-1-7006 | 7.9 | 9.5 | 11.1 | 14.3 | 17.4 | 22.2 | 27.0 | 31.7 | 3.9 |
| Ammonio methacrylate copolymer dispersion, Type B, 30% dispersion (Eudragit RS30D Solids), NF | 21.3 | 25.6 | 29.9 | 38.4 | 47.0 | 59.8 | 72.6 | 85.4 | 10.5 |
| Triethyl Citrate, USP/NF | 3.3 | 3.9 | 4.6 | 5.9 | 7.2 | 9.1 | 11.1 | 13.0 | 1.6 |
| Glyceryl monostearate emulsion (Plasacryl T20), HS, solids | 5.5 | 6.6 | 7.7 | 9.9 | 12.1 | 15.4 | 18.7 | 22.0 | 2.7 |

TABLE 15-continued

Composition of the dosage form (Formulation I 80:20) MPH IR distal:

| Ingredient | Quantity per capsule (mg) per Strength (label claim) approx: | | | | | | | | |
|---|---|---|---|---|---|---|---|---|---|
| | 25 mg | 30 mg | 35 mg | 45 mg | 55 mg | 70 mg | 85 mg | 100 mg | % |
| Silicon dioxide, (Syloid 244FP), NF | 1.0 | 1.2 | 1.4 | 1.8 | 2.2 | 2.8 | 3.5 | 4.1 | 0.5 |
| Eudragit FS30D, HS, solids | 32.1 | 38.5 | 45.0 | 57.8 | 70.7 | 89.9 | 109.2 | 128.5 | 15.8 |
| TOTAL (approx.) | 203 | 244 | 285 | 366 | 447 | 569 | 691 | 813 | 100 |

TABLE 16

Composition of the dosage form (Formulation J 80:20) MPH IR distal:

| Ingredient | Quantity per capsule (mg) per Strength (label claim) approx: | | | | | | | | |
|---|---|---|---|---|---|---|---|---|---|
| | 25 mg | 30 mg | 35 mg | 45 mg | 55 mg | 70 mg | 85 mg | 100 mg | % |
| Methylphenidate HCl, USP | 25 | 30 | 35 | 45 | 55 | 70 | 85 | 100 | 18.4 |
| Sugar spheres 14/18 mesh, USP/NF | 60.8 | 72.9 | 84.9 | 109.5 | 133.7 | 169.9 | 206.5 | 243.1 | 44.7 |
| Opadry Clear YS-1-7006 | 8.0 | 9.6 | 11.2 | 14.5 | 17.6 | 22.4 | 27.3 | 32.2 | 5.9 |
| Ammonio methacrylate copolymer dispersion, Type B, 30% dispersion (Eudragit RS30D Solids), NF | 14.0 | 16.8 | 19.6 | 25.2 | 30.8 | 39.1 | 47.6 | 55.55 | 10.3 |
| Triethyl Citrate, USP/NF | 2.2 | 2.6 | 3.0 | 3.9 | 4.8 | 6.1 | 7.4 | 8.61 | 1.6 |
| Glyceryl monostearate emulsion (Plasacryl T20), HS, solids | 3.5 | 4.3 | 4.9 | 6.4 | 7.8 | 9.9 | 12.0 | 14.1 | 2.6 |
| Silicon dioxide, (Syloid 244FP), NF | 1.1 | 1.3 | 1.5 | 2.0 | 2.4 | 3.0 | 3.7 | 4.52 | 0.8 |
| Eudragit FS30D, HS, solids | 21.2 | 25.4 | 29.6 | 38.2 | 46.6 | 59.3 | 72.1 | 84.61 | 15.6 |
| TOTAL (approx.) | 136 | 163 | 190 | 245 | 299 | 380 | 462 | 543 | 100 |

What is claimed is:

1. A method of treating Attention Deficit Hyperactivity Disorder (ADHD) in a subject in need thereof, the method comprising administering to the subject an oral solid pharmaceutical composition comprising an immediate release methylphenidate hydrochloride component and a controlled/delayed release methylphenidate hydrochloride component, wherein the immediate release methylphenidate component and the controlled/delayed release methylphenidate component, together, provide 25, 35, 45, 55, 70, 85, or 100 mg of methylphenidate hydrochloride; and wherein the oral solid pharmaceutical composition, when administered to a subject in a fed state, provides at least two pharmacokinetic parameters selected from the group consisting of:
an average±standard deviation methylphenidate $AUC_{0-4}$ of 21160.21±6420.56 pg·hr/mL;
an average±standard deviation methylphenidate $AUC_{8-12}$ of 29392.15±8453.72 pg·hr/mL;
an average±standard deviation methylphenidate $AUC_{12-16}$ of 36653.88±11521.14 pg·hr/mL;
an average±standard deviation methylphenidate $AUC_{0-16}$ of 113468.45±26835.93 pg·hr/mL;
an average±standard deviation methylphenidate $AUC_{0-12}$ of 76814.57±16722.84 pg·hr/mL;
an average±standard deviation methylphenidate $AUC_{12-t}$ of 84456.90±26718.88 pg·hr/mL;
an average±standard deviation methylphenidate $C_{max0-4}$ of 9248.95±1886.65 pg/mL; and
an average±standard deviation methylphenidate $C_{max8-16}$ of 10667.64±3017.29 pg/mL;
when the oral solid pharmaceutical composition provides 100 mg of methylphenidate hydrochloride, or dose proportional AUC or $C_{max}$ values thereof, when the oral solid pharmaceutical composition provides 25, 35, 45, 55, 70, or 85 mg methylphenidate hydrochloride;
wherein the oral solid pharmaceutical composition provides efficacious treatment of ADHD for 16 hours after a single oral administration; and further wherein the oral solid pharmaceutical composition has the following in vitro methylphenidate dissolution profile:

| Time (hours) | Methylphenidate (% dissolved) |
|---|---|
| 1 | NLT 15% |
| 4 | 18-38% |
| 8 | 35-55% |
| 12 | 68-98 |
| 16 | NLT 68 | when tested according to the USP paddle oral solid pharmaceutical composition, 100 rpm, at 37° C.; (i) starting with 900 ml simulated gastric fluid for 2 hours, (ii) followed by 900 ml phosphate buffer pH 6.0 for 4 hours, and (iii) for the 7th hour onwards, 900 mL of phosphate buffer pH 7.4; USP <711> Acceptance Table 2.

2. The method of claim 1, wherein the controlled/delayed release methylphenidate hydrochloride component and the immediate release methylphenidate component are provided via a plurality of coated beads.

3. The method of claim 2, wherein each bead comprises a portion of the controlled/delayed release methylphenidate hydrochloride component and a portion of the immediate release methylphenidate component.

4. The method of claim 3, wherein each bead in the plurality of beads comprises a core comprising a first amount of methylphenidate hydrochloride corresponding to the portion of the delayed/controlled release methylphenidate hydrochloride component.

5. The method of claim 4, wherein the core comprises a granule coated with the first amount of methylphenidate hydrochloride or wherein the core comprises a granule substrate in admixture with the first amount of methylphenidate hydrochloride.

6. The method of claim 5, wherein the core comprises the granule coated with the first amount of methylphenidate hydrochloride.

7. The method of claim 6, wherein the first amount of methylphenidate hydrochloride is coated with an inner controlled release coating and an outer delayed release coating coated over the inner controlled release coating.

8. The method of claim 7, wherein a second amount of methylphenidate hydrochloride, corresponding to the portion of the immediate release methylphenidate component, is coated over the outer delayed release coating.

9. The method of claim 8, wherein the delayed/controlled release methylphenidate hydrochloride component comprises about 78 weight percent to about 82 weight percent of the 25, 35, 45, 55, 70, 85, or 100 mg of methylphenidate hydrochloride in the pharmaceutical composition.

10. The method of claim 9, wherein the delayed/controlled release methylphenidate hydrochloride component comprises about 80 weight percent of the 25, 35, 45, 55, 70, 85, or 100 mg of methylphenidate hydrochloride in the pharmaceutical composition and wherein the immediate release methylphenidate component provides about 20 percent by weight of the 25, 35, 45, 55, 70, 85, or 100 mg methylphenidate hydrochloride in the pharmaceutical composition.

11. The method of claim 6, wherein the granule is selected from the group consisting of: a sugar sphere, a microcrystalline cellulose granule, a silica granule, a starch granule, a lactose granule, a calcium carbonate granule, and a mannitol-polyvinylpyrrolidone granule.

12. The method of claim 7, wherein the inner controlled release coating is present in an amount of about 3 percent to about 16 percent by weight of each bead in the plurality of coated beads, and wherein the outer delayed release coating is present in an amount of from about 3 percent to about 20 percent by weight of each bead in the plurality of coated beads.

13. The method of claim 12, wherein the inner controlled release coating is present in an amount of about 10.0 percent to about 10.7 percent by weight of each bead in the plurality of coated beads, and wherein the outer delayed release coating is present in an amount of from about 15 percent to about 16 percent by weight of each bead in the plurality of coated beads.

14. The method of claim 13, wherein the inner controlled release coating comprises ammonio methacrylate copolymer, Type B USP/NF.

15. The method of claim 14, wherein the outer delayed release coating comprises poly(methyl acrylate-co-methyl methacrylate-co-methacrylic acid) 7:3:1.

16. A method of treating Attention Deficit Hyperactivity Disorder (ADHD) in a subject in need thereof, the method comprising administering to the subject an oral solid pharmaceutical composition comprising an immediate release methylphenidate hydrochloride component and a controlled/delayed release methylphenidate hydrochloride component, wherein the immediate release methylphenidate component and the controlled/delayed release methylphenidate component, together, provide 25, 35, 45, 55, 70, 85, or 100 mg of methylphenidate hydrochloride; and wherein the oral solid pharmaceutical composition, when administered to a subject in a fasted state, provides at least two pharmacokinetic parameters selected from the group consisting of:

an average±standard deviation methylphenidate $AUC_{0-4}$ of 24818.34±7976.76 pg·hr/mL;

an average±standard deviation methylphenidate $AUC_{8-12}$ of 36457.19±18489.84 pg·hr/mL;

an average±standard deviation methylphenidate $AUC_{12-16}$ of 39322.95±10236.29 pg·hr/mL;

an average±standard deviation methylphenidate $AUC_{0-16}$ of 124407.07±40902.66 pg·hr/mL;

an average±standard deviation methylphenidate $AUC_{0-12}$ of 85084.12±33395.48 pg·hr/mL;

an average±standard deviation methylphenidate $AUC_{12-t}$ of 82699.74±21862.39 pg·hr/mL;

an average±standard deviation methylphenidate $C_{max0-4}$ of 9365.42±3213.96 pg/mL; and an average±standard deviation methylphenidate $C_{max8-16}$ of 12413.97±4546.66 pg/mL;

when the oral solid pharmaceutical composition provides 100 mg of methylphenidate hydrochloride, or dose proportional AUC values thereof, or dose proportional $C_{max}$ values thereof, when the oral solid pharmaceutical composition provides 25, 35, 45, 55, 70, or 85 mg methylphenidate hydrochloride;

wherein the oral solid pharmaceutical composition provides efficacious treatment of ADHD for 16 hours after a single oral administration; and further wherein the oral solid pharmaceutical composition has the following in vitro methylphenidate dissolution profile:

| Time (hours) | Methylphenidate (% dissolved) |
| --- | --- |
| 1 | NLT 15% |
| 4 | 18-38% |
| 8 | 35-55% |
| 12 | 68-98 |
| 16 | NLT 68 | when tested according to the USP paddle oral solid pharmaceutical composition, 100 rpm, at 37° C.; (i) starting with 900 ml simulated gastric fluid for 2 hours, (ii) followed by 900 ml phosphate buffer pH 6.0 for 4 hours, and (iii) for the 7th hour onwards, 900 mL of phosphate buffer pH 7.4; USP <711> Acceptance Table 2.

17. The method of claim 16, wherein the controlled/delayed release methylphenidate hydrochloride component and the immediate release methylphenidate component are provided via a plurality of coated beads.

18. The method of claim 17, wherein each bead comprises a portion of the controlled/delayed release methylphenidate hydrochloride component and a portion of the immediate release methylphenidate component.

19. The method of claim 18, wherein each bead in the plurality of beads comprises a core comprising a first amount of methylphenidate hydrochloride corresponding to the portion of the delayed/controlled release methylphenidate hydrochloride component.

20. The method of claim 19, wherein the core comprises a granule coated with the first amount of methylphenidate hydrochloride or wherein the core comprises a granule substrate in admixture with the first amount of methylphenidate hydrochloride.

21. The method of claim 20, wherein the core comprises the granule coated with the first amount of methylphenidate hydrochloride.

22. The method of claim 21, wherein the first amount of methylphenidate hydrochloride is coated with an inner controlled release coating and an outer delayed release coating coated over the inner controlled release coating.

23. The method of claim 22, wherein a second amount of methylphenidate hydrochloride, corresponding to the portion of the immediate release methylphenidate component, is coated over the outer delayed release coating.

24. The method of claim 23, wherein the delayed/controlled release methylphenidate hydrochloride component comprises about 78 weight percent to about 82 weight percent of the 25, 35, 45, 55, 70, 85, or 100 mg of methylphenidate hydrochloride in the pharmaceutical composition.

25. The method of claim 24, wherein the delayed/controlled release methylphenidate hydrochloride component comprises about 80 weight percent of the 25, 35, 45, 55, 70, 85, or 100 mg of methylphenidate hydrochloride in the pharmaceutical composition and wherein the immediate release methylphenidate component provides about 20 percent by weight of the 25, 35, 45, 55, 70, 85, or 100 mg methylphenidate hydrochloride in the pharmaceutical composition.

26. The method of claim 21, wherein the granule is selected from the group consisting of: a sugar sphere, a microcrystalline cellulose granule, a silica granule, a starch granule, a lactose granule, a calcium carbonate granule, and a mannitol-polyvinylpyrrolidone granule.

27. The method of claim 22, wherein the inner controlled release coating is present in an amount of about 3 percent to about 16 percent by weight of each bead in the plurality of coated beads, and wherein the outer delayed release coating is present in an amount of from about 3 percent to about 20 percent by weight of each bead in the plurality of coated beads.

28. The method of claim 27, wherein the inner controlled release coating is present in an amount of about 10.0 percent to about 10.7 percent by weight of each bead in the plurality of coated beads, and wherein the outer delayed release coating is present in an amount of from about 15 percent to about 16 percent by weight of each bead in the plurality of coated beads.

29. The method of claim 28, wherein the inner controlled release coating comprises ammonio methacrylate copolymer, Type B USP/NF.

30. The method of claim 29, wherein the outer delayed release coating comprises poly(methyl) acrylate-co-methyl methacrylate-co-methacrylic acid) 7:3:1.

\* \* \* \* \*

UNITED STATES PATENT AND TRADEMARK OFFICE
CERTIFICATE OF CORRECTION

PATENT NO. : 10,512,613 B2  
APPLICATION NO. : 16/399580  
DATED : December 24, 2019  
INVENTOR(S) : Vargas Rincon et al.

Page 1 of 1

It is certified that error appears in the above-identified patent and that said Letters Patent is hereby corrected as shown below:

In the Claims

1. Column 34, Claim 4, Line 66, "the delayed/controlled release" should read -- the controlled/delayed release --.

2. Column 35, Claim 9, Lines 18, "the delayed/controlled release" should read -- the controlled/delayed release --.

3. Column 35, Claim 10, Line 23, "the delayed/controlled release" should read -- the controlled/delayed release --.

4. Column 36, Claim 19, Lines 61, "the delayed/controlled release" should read -- the controlled/delayed release --.

5. Column 37, Claim 24, Lines 12, "the delayed/controlled release" should read -- the controlled/delayed release --.

6. Column 37, Claim 25, Lines 18, "the delayed/controlled release" should read -- the controlled/delayed release --.

Signed and Sealed this  
Eighteenth Day of February, 2020

Andrei Iancu  
*Director of the United States Patent and Trademark Office*